(12) United States Patent
Hirszowicz et al.

(10) Patent No.: US 8,197,505 B2
(45) Date of Patent: Jun. 12, 2012

(54) BALLOON CATHETER SYSTEM FOR TREATING VASCULAR OCCLUSIONS

(75) Inventors: Eran Hirszowicz, Ramat Gan (IL); Eran Levit, Kfar Vradim (IL); Shay Dubi, Tel Aviv (IL)

(73) Assignee: Endocross Ltd., Yokneam (IL)

( * ) Notice: Subject to any disclaimer, the term of this patent is extended or adjusted under 35 U.S.C. 154(b) by 574 days.

(21) Appl. No.: 12/292,597

(22) Filed: Nov. 21, 2008

(65) Prior Publication Data

US 2009/0171278 A1 Jul. 2, 2009

Related U.S. Application Data

(63) Continuation-in-part of application No. 11/546,571, filed on Oct. 12, 2006, now abandoned.

(60) Provisional application No. 60/726,180, filed on Oct. 14, 2005, provisional application No. 60/800,035, filed on May 15, 2006.

(51) Int. Cl.
*A61M 29/00* (2006.01)

(52) U.S. Cl. ..................................... 606/194

(58) Field of Classification Search ............ 604/96.01, 604/101.01, 915; 606/192–194
See application file for complete search history.

(56) References Cited

U.S. PATENT DOCUMENTS

| | | | |
|---|---|---|---|
| 4,781,681 A | 11/1988 | Sharrow | |
| 5,318,532 A | 6/1994 | Frassica | |
| 5,733,260 A | 3/1998 | De Maio | |
| 5,782,760 A * | 7/1998 | Schaer | 600/381 |
| 5,810,871 A * | 9/1998 | Tuckey et al. | 606/198 |
| 6,221,043 B1 * | 4/2001 | Fischell et al. | 604/103.07 |
| 7,322,958 B2 * | 1/2008 | Wholey et al. | 604/102.01 |
| 2005/0038382 A1 | 2/2005 | Miller et al. | |

FOREIGN PATENT DOCUMENTS

EP 0 540 858 A1 5/1993

OTHER PUBLICATIONS

PCT/IL2007/000590 Search Report dated Sep. 14, 2007.

* cited by examiner

*Primary Examiner* — Manuel Mendez
(74) *Attorney, Agent, or Firm* — Venable LLP; Michele V. Frank

(57) ABSTRACT

The present invention provides a balloon catheter comprising:
  a hollow inner shaft disposed within a hollow outer shaft;
  a balloon attached at its proximal end to said outer shaft and at its distal end to said inner shaft;
  wherein the inner shaft is constructed such that following radial expansion of the balloon to a first expanded state, said inner shaft is capable of responding to further longitudinal expansion of the balloon to a second expanded state by increasing its length from a resting value, and of responding to subsequent partial deflation back to said first expanded state by reducing its length back to said resting value.

32 Claims, 14 Drawing Sheets

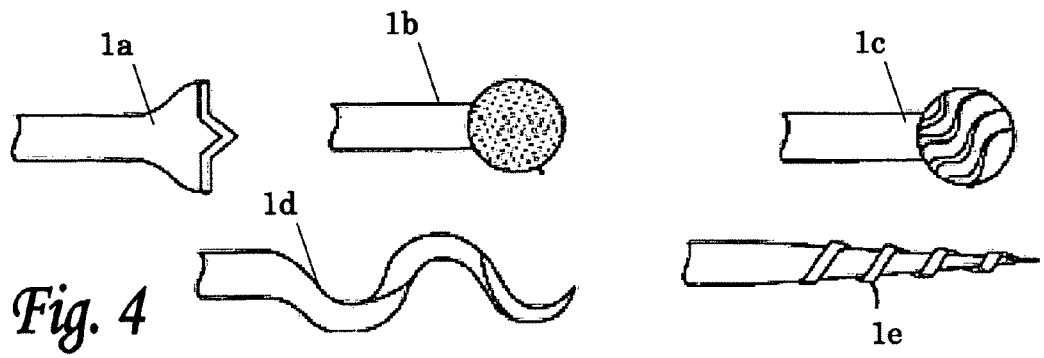
Fig. 4
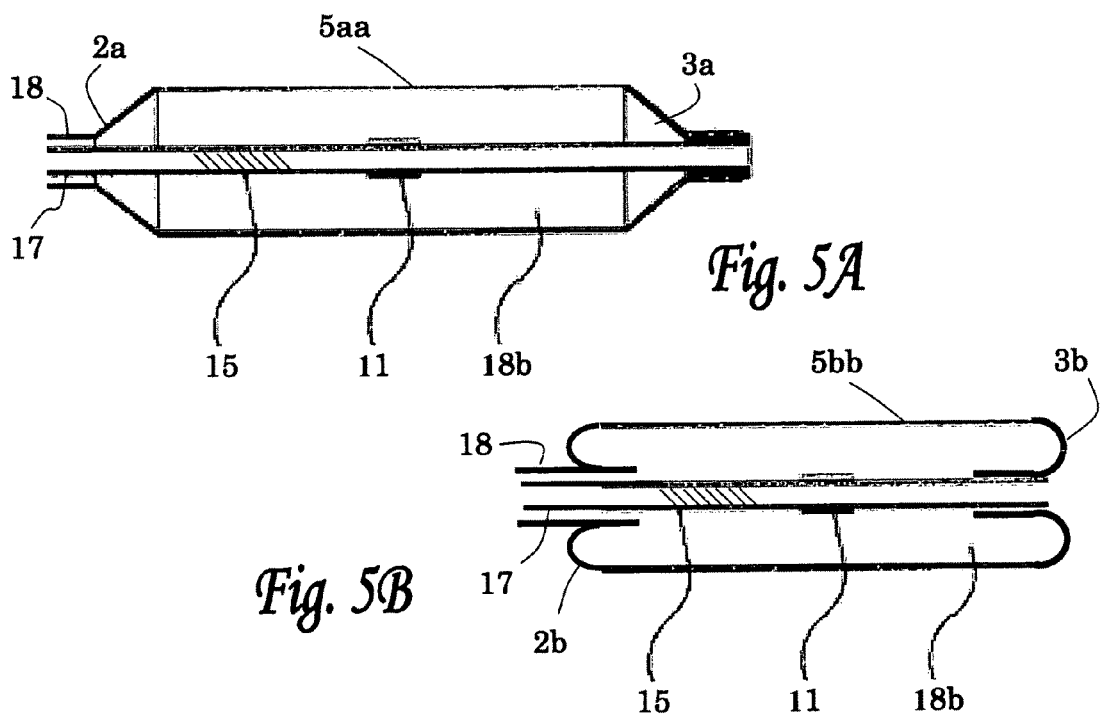
Fig. 5A
Fig. 5B
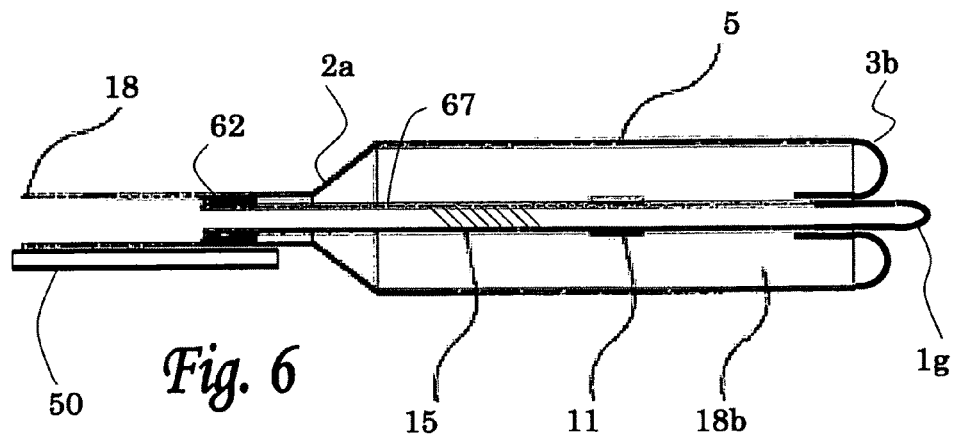
Fig. 6

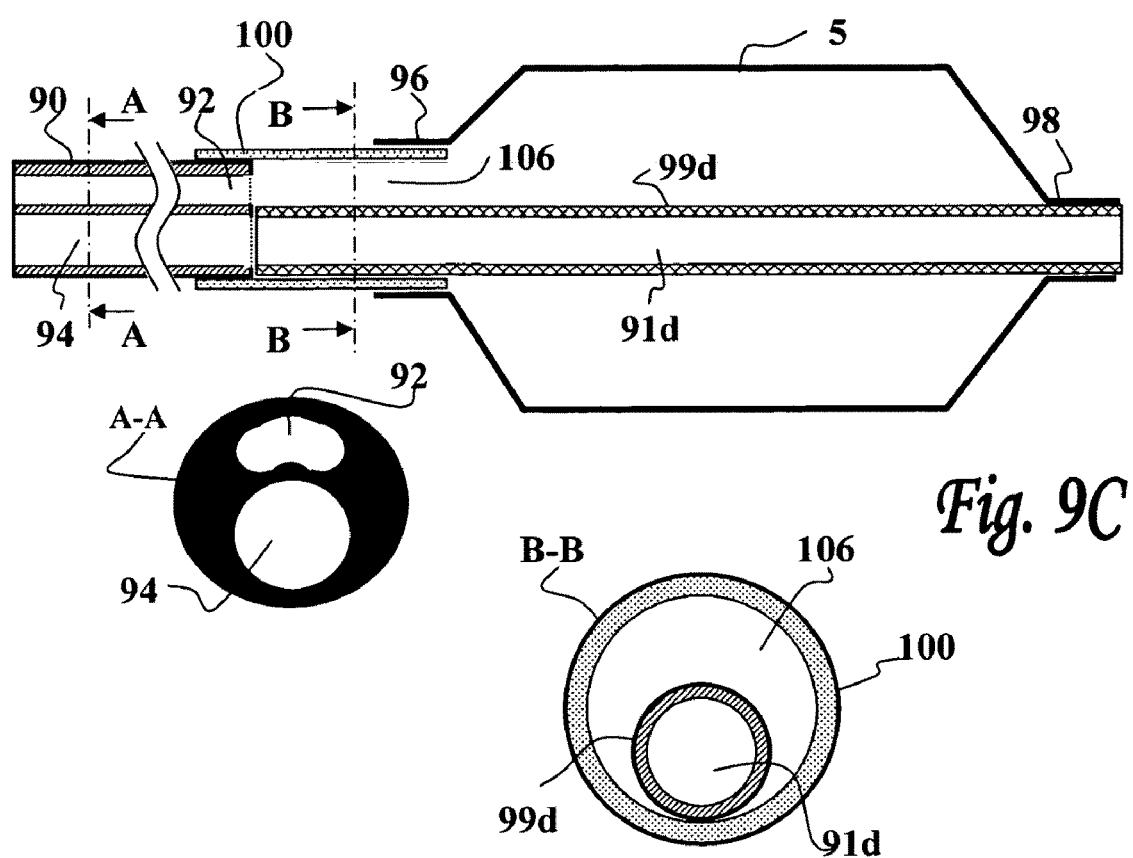

BALLOON CATHETER SYSTEM FOR TREATING VASCULAR OCCLUSIONS

This application is a continuation-in-part of application Ser. No. 11/546,571, filed Oct. 12, 2006, which claims priority to U.S. provisional Application Nos. 60/726,180 and 60/800,035, filed Oct. 14, 2005 and May 15, 2006, and International Application No. PCT/IL2007/000590 filed 14 May 2007, the entire contents of each of which are hereby incorporated by reference.

FIELD OF THE INVENTION

The present invention relates to balloon catheter systems. More specifically, the present invention provides crossing balloon systems (CBS) for use in the treatment of chronic total occlusion (CTO) and related conditions in blood vessels.

BACKGROUND OF THE INVENTION

Chronic total occlusion of a blood vessel is, as the name suggests, a condition in which there is complete (or near complete) obstruction of that vessel due to the development of an intravascular lesion comprising atheromatous plaque material and/or thrombic material. Between 10 and 20 percent of patients undergoing percutaneous coronary interventions (PCI) have CTO. Successful opening of CTO lesions improves anginal status, increases exercise capacity, and reduces the need for bypass surgery. However, PCI of cases of CTO have historically posed problems, with lower success rates (40 to 80 percent-average 60 percent), higher equipment costs, and a higher restenosis rate. When MACE (Major Arterial or Cardiac Events) is taken into account, the success rate typically in the range of 20 to 30 percent.

Conventional intervention tools such as angioplasty balloons are often too flexible or blunt to cross the CTO site, which often contains extremely hard, calcified tissue that may form an impenetrable barrier to the advancement of a guidewire therethrough. Even a less than total occlusion may contain complex structures which may trap or divert the steering end of the guidewire. In view of the great difficulties encountered in attempting to properly position a guidewire across the stenosis, conventional guided atherectomy or dilatation devices such as cutting elements and balloons cannot be used to cross the lesion as long as a guidewire was not inserted through the lesion since they rely on complete wire crossability.

A further problem associated with the use of conventional devices is the risk of perforating the blood vessel being treated. For example, a guidewire or cutting tool, when advanced, may cause dissection of the tissues of the arterial wall instead of the occlusion, thereby creating a false lumen and possibly perforating the artery. If enough blood from a perforated artery accumulates in the pericardial space surrounding the heart, it will result in a condition known as cardiac tamponade in which the heart is compressed and emergency surgical intervention is required to avert heart failure and death.

Another reason that conventional types of apparatus are typically ineffective in treating total or near total occlusions is that conventional balloon catheter shafts and guidewires do not perform well under the compressive loading and torque loading that are required in order to advance such devices across a CTO lesion.

Statistically, the predominant reason for failure to open CTO lesions with PCI has been failure to cross the lesion with a guidewire (80 percent) and failure of a balloon to track along the guidewire (15 percent) through the very hard lesion. Many types of guidewires and devices have been tried, but successful recanalization has remained at about 60 percent. Crossing CTO lesions in patients with peripheral vascular disease has met with similar problems, for example, the reported success rate for percutaneous catheter-based treatment of chronic subclavian artery occlusion being in the range of 46%-83%.

It is therefore an object of the present invention to provide a balloon catheter system that is capable of penetrating and crossing CTO lesions.

Another object of the present invention is to provide a CTO-crossing system that will minimize trauma to the vascular wall.

A further object of the present invention is to provide a balloon catheter system having the aforementioned advantages together with the additional advantage of being relatively easy to operate in the hands of healthcare professionals with experience with conventional atherectomy and dilation systems.

Further objects and advantages of the present invention will become apparent as the description proceeds.

SUMMARY OF THE INVENTION

It has now been found by the inventors that it is possible to achieve the above-mentioned objectives by means of the use of a balloon catheter system fitted with a balloon that is terminally infolded (or a balloon which may be caused to adopt such an intussuscepted configuration). Following delivery of the balloon to the proximal side of the occluding vascular lesion to be treated, said balloon is inflated such that it becomes anchored within the blood vessel. The balloon is then caused to rapidly inflate and partially deflate in a cyclic manner, such that said balloon alternately elongates and axially contracts. The distal portion of the catheter shaft upon which the balloon is mounted, and/or a guide wire that projects beyond the distal end of said catheter shaft is thereby caused to similarly oscillate along a distal-proximal axis (wherein proximal is defined as the direction towards the operator and distal as the direction away from the operator). This longitudinal oscillation of the catheter shaft and/or guide wire in proximity to the occluding lesion to be treated causes damage and break-up of the lesion, ultimately enabling the operator to advance the balloon catheter and/or other conventional angioplasty devices across the lesion.

During the course of their work, the inventors further found that in order to facilitate oscillation of the catheter shaft along a distal-proximal axis in response to the similar elongation-contraction of the balloon, it is desirable that said catheter shaft contains at least one portion that is elastically deformable along said distal-proximal axis. Without wishing to be bound by theory, it is believed that in response to increased pressure inside the proximally intussuscepted balloon, the folded distal balloon tapers are extended in a distal direction thereby exerting tension forces along the catheter shaft. Due to the elasticity of the shaft, the induced tension forces result in elongation of the said shaft, thereby stressing the shaft, similar to a tension spring charging procedure. Partial pressure release inside the balloon reduces these tension forces. The catheter shaft then acts as a returning spring and thereby assists in rolling the distal balloon tapers back to their initial position.

The present invention is therefore primarily directed to a balloon catheter comprising:

a hollow inner shaft disposed within a hollow outer shaft such that the distal end of the inner shaft extends beyond the distal end of the outer shaft, wherein the lumen of said inner shaft is suitable for allowing the passage of a guidewire through all or part of its length;

a balloon attached at its proximal end to said outer shaft and at its distal end to said inner shaft; and means for the introduction of an inflation fluid into the annular space formed between the inner surface of the outer shaft and the outer surface of the inner shaft and therefrom into the lumen of said balloon, and for the removal thereof;

wherein the inner shaft is constructed such that following radial expansion of the balloon to a first expanded state, said inner shaft is capable of responding to further longitudinal expansion of the balloon to a second expanded state by increasing its length from a resting value, and of responding to subsequent partial deflation back to said first expanded state by reducing its length back to said resting value.

In one preferred embodiment of the invention, the inner shaft of the balloon catheter defined hereinabove comprises at least one portion that is elastically deformable.

In one preferred embodiment of the balloon catheter described hereinabove, following radial expansion of the balloon to a first expanded state, said elastically deformable portion of the inner shaft is capable of responding to further longitudinal expansion of the balloon to a second expanded state by increasing its length from a resting value, and of responding to subsequent partial deflation back to said first expanded state by reducing its length back to said resting value.

According to one preferred embodiment of the balloon catheter of the invention, the distance between the points of attachment of the balloon to the inner and outer shafts is less than the overall length of the balloon.

According to another preferred embodiment of the balloon catheter defined hereinabove, the balloon is attached at its distal end in an inverted manner, such that the external surface of said balloon is in contact with, and attached to, the outer surface of the inner shaft.

In yet another preferred embodiment, the balloon is attached at its distal end in a non-inverted manner, such that the internal surface of said balloon is in contact with, and attached to, the outer surface of the inner shaft.

In one particularly preferred embodiment, the aforementioned at least one elastically deformable portion is constructed of a blend of nylon and Pebax.

The balloon catheter defined hereinabove may be constructed either in the form of an over-the-wire catheter or as a rapid exchange (single operator) catheter. Both of these embodiments will be described in detail hereinbelow.

In another preferred embodiment of the invention, the balloon catheter disclosed hereinabove, the inner shaft is capable of being moved along its longitudinal axis in relation to the outer shaft, and wherein said catheter further comprises means for immobilizing said inner shaft.

The present invention also provides a balloon catheter comprising a conduit having a proximal and a distal portion,
wherein said proximal portion contains two separate lumens, one of said lumens being suitable for allowing the passage of a guidewire therethrough, the other lumen being suitable for allowing passage of a fluid,
wherein said distal portion is a single-lumen conduit that is in fluid communication with the guidewire lumen of said proximal portion
wherein a balloon is attached at its proximal end to the outer surface of said proximal portion and at its distal end to said distal portion,
and wherein at least part of said distal portion is constructed such that following radial expansion of the balloon to a first expanded state, said distal conduit portion is capable of responding to further expansion of the balloon to a second expanded state by increasing its length from a resting value, and of responding to subsequent partial deflation back to said first expanded state by reducing its length back to said resting value.

In a particularly preferred embodiment of the device disclosed immediately hereinabove, the distal portion of the conduit comprises at least one portion that is elastically deformable. In a particularly preferred embodiment of this implementation, the at least one elastically deformable portion is constructed of a blend of nylon and Pebax.

The present invention also provides the following modifications of the embodiment described immediately hereinabove, in which the length of the flexible distal portion need not be limited to the length of the balloon as is the case in said embodiment.

In the first of these modifications, the proximal balloon neck is longer than in the previously-described embodiment (and indeed is substantially longer than the proximal balloon neck of conventional angioplastic balloons) thereby permitting the use of a longer distal portion within the abovementioned conduit construction.

In the second of these modifications, the catheter further comprises a connecting tube segment positioned between the conduit proximal portion and the proximal balloon neck, thereby forming a middle portion, wherein said middle portion comprises two concentrically arranged conduits, the lumen of the outer of said concentrically arranged conduits being in fluid communication with the fluid passage lumen of said proximal portion, the inner of said concentrically arranged conduits being formed by the distal conduit, wherein the lumen of said distal conduit is in fluid communication with the guidewire lumen of said proximal portion, the connecting tube segment having a proximal end attached to the distal end of the proximal portion, and a distal end attached to the balloon proximal neck.

In particularly preferred embodiments of both of the modifications of the previously-described implementation, the distal portion comprises at least one portion that is elastically deformable. In a particularly preferred embodiment of this implementation, the at least one elastically deformable portion is constructed of a blend of nylon and Pebax.

In another aspect, the present invention is directed to a method for treating vascular occlusions in a patient in need of such treatment, comprising the steps of:

a) bringing a balloon into proximity with a vascular occlusion within a blood vessel to be treated;

b) causing said balloon to be cyclically inflated and partially deflated such that an element attached to said balloon is caused to oscillate along a distal-proximal axis in close proximity to the vascular occlusion, thereby causing complete or partial fracture of said occlusion.

In a particularly preferred embodiment of this method, the element attached to the balloon is a portion of a catheter shaft. Preferably, this portion is the distal most portion of the catheter (i.e. the inner shaft of the first embodiment described hereinabove, or the distal portion of the conduit described in the immediately preceding two embodiments). In another particularly preferred embodiment, the element attached to the balloon is a guidewire immobilized within a catheter shaft.

Preferably, prior to the cyclical inflation and partial deflation of the balloon, said balloon is inflated to a first pressure, such that said balloon becomes anchored within the blood vessel being treated, and such that during the step of cyclical inflation and partial deflation, the balloon is further inflated by increasing its internal pressure from said first pressure to a second pressure, and partially deflated by reducing its internal pressure from said second pressure to said first pressure.

In one implementation of the method of the present invention, subsequent to anchoring of the balloon within the blood vessel, said method further comprises the step of moving the inner catheter shaft in a proximal direction such that the distal extremity of the balloon becomes intussuscepted. This particular embodiment of the method of the invention is generally used in conjunction with balloons that are manufactured such that they do not inherently possess an intussuscepted portion ("non-charged" balloons, as described in more detail hereinafter) The proximal movement of the inner shaft, as mentioned above, thereby causes the formation of an intussusception in the previously non-intussuscepted balloon.

The present invention also provides a second main group of embodiments of the basic device disclosed hereinabove. The key feature of this group of devices is the presence of means for grasping and immobilizing a guidewire placed within a guidewire lumen, such that the distal tip of said guidewire extends beyond the distal extremity of the guidewire lumen. The guidewire grasping and immobilizing means is provided by an elastically deformable region of the wall of the guidewire conduit. This elastically deformable region is distinct from the elastically deformable region described hereinabove, the purpose of which is to permit alternate elongation and axial contraction of the inner shaft in response to cyclic inflation/partial deflation of the balloon. It is to be emphasized that in this group of embodiments, the distal portion of the guidewire conduit contains at least two distinct elastically-deformable regions. The first of these regions responds to elevation of the fluid pressure within the catheter to a first pressure increment by means of reducing its diameter, thereby applying a 'strangling' force on the guidewire. The second of these regions (while remaining non-responsive to the first pressure increment) responds to further elevation of the fluid pressure by a second, higher pressure increment (and associated elongation of the balloon) by means of axial elongation, and subsequent contraction upon reduction of the pressure by an amount equal to the second pressure increment. The catheter devices in this group of embodiments may further comprise supplementary guidewire grasping elements, as will be disclosed and described hereinafter.

Thus, in another aspect, the present invention provides a balloon catheter comprising:
  an inner shaft disposed within an outer shaft such that the distal end of the inner shaft extends beyond the distal end of the outer shaft, wherein the lumen of said inner shaft is suitable for allowing the passage of a guidewire through all or part of its length;
  a balloon attached at its proximal end to said outer shaft and at its distal end to said inner shaft; and
  means for the introduction of an expansion fluid into the annular space formed between the inner surface of the outer shaft and the outer surface of the inner shaft and therefrom into the lumen of said balloon, and for the removal thereof;
  wherein the inner shaft is constructed such that following radial expansion of the balloon to a first expanded state, a portion of said inner shaft is capable of responding to further longitudinal expansion of the balloon to a second expanded state by reducing its inner diameter thereby being able to grasp a guidewire placed within the lumen of said inner shaft, thereby preventing movement of said guidewire relative to said inner shaft, and such that
  said inner shaft is capable of responding to further expansion of the balloon from said second expanded state to a third expanded state by increasing its length from a resting value, and of responding to subsequent partial deflation back to said second expanded state by reducing its length back to said resting value.

In one preferred embodiment, the inner shaft comprises at least a first elastically deformable portion and second elastically deformable portion, wherein, following radial expansion of the balloon to a first expanded state,
  said first elastically deformable portion of the shaft is capable of responding to further longitudinal expansion of the balloon to a second expanded state by reducing its inner diameter thereby being able to grasp a guidewire placed within the lumen of said inner shaft and thereby preventing movement of said guidewire relative to said inner shaft,
  and wherein said second elastically deformable portion of the shaft is capable of responding to further longitudinal expansion of the balloon from said second expanded state to a third expanded state by increasing its length from a resting value, and of responding to subsequent partial deflation back to said second expanded state by reducing its length back to said resting value.

In one preferred embodiment, the distance between the points of attachment of the balloon to the inner and outer shafts is less than the overall length of the balloon when said balloon is in the first expanded state.

In another particularly preferred embodiment, the first and second elastically deformable portions are each constructed of blends of nylon and Pebax.

In a further preferred embodiment of the invention, the balloon catheter further comprises supplementary guide wire grasping means. It is possible to use any suitable mechanical elements for implementing these supplementary means. In one preferred embodiment, however, the supplementary guidewire grasping means comprise protrusions on the inner wall of the inner shaft. In another preferred embodiment, the supplementary guide wire grasping means comprise wedge-shaped locking elements.

Various balloon attachment configurations may be used in implementing this group of embodiments of the invention. Thus, in one preferred embodiment, the balloon is attached at its distal end in an inverted manner, such that the external surface of said balloon is in contact with, and attached to, the outer surface of the inner shaft. In another preferred embodiment, the balloon is attached at its distal end in a non-inverted manner, such that the internal surface of said balloon is in contact with, and attached to, the outer surface of the inner shaft.

The presently-disclosed embodiments of the balloon catheter of the present invention may be constructed either in the form of an over-the-wire catheter or as a rapid exchange (single operator) catheter. Both of these embodiments will be described in detail hereinbelow.

In one preferred embodiment of the catheter of the present invention, the inner shaft is capable of being moved along its longitudinal axis in relation to the outer shaft, said catheter further comprising means for immobilizing said inner shaft.

The present invention further provides a balloon catheter comprising a conduit having proximal and distal portions,
  wherein said proximal portion contains two separate lumens, one of said lumens being suitable for allowing the passage of a guidewire therethrough, the other lumen being suitable for allowing passage of a fluid,
  wherein said distal portion contains a single lumen, said lumen being the continuation of the guidewire lumen, wherein a balloon is attached at its proximal end to said proximal conduit portion and at its distal end to said distal conduit portion;

and wherein the distal portion of the conduit is constructed such that following radial expansion of the balloon to a first expanded state, a portion of said distal conduit portion is capable of responding to further longitudinal expansion of the balloon to a second expanded state by reducing its inner diameter thereby being able to grasp a guidewire placed within the lumen of said distal conduit portion, thereby preventing movement of said guidewire relative to said inner shaft, and such that said distal conduit portion is capable of responding to further expansion of the balloon from said second expanded state to a third expanded state by increasing its length from a resting value, and of responding to subsequent partial deflation back to said second expanded state by reducing its length back to said resting value.

The present invention also provides a balloon catheter comprising a conduit having a proximal portion, a middle portion and a distal portion, wherein said proximal portion contains two separate lumens, one of said lumens being suitable for allowing the passage of a guidewire therethrough, the other lumen being suitable for allowing passage of a fluid, wherein said middle portion contains two concentrically arranged conduits, the lumen of the outer conduit being in fluid communication with the fluid passage lumen of said proximal portion, the lumen of the inner conduit being in fluid communication with the guidewire lumen of said proximal portion, wherein said distal portion is a single-lumen conduit that is in fluid communication with the inner lumen of said middle portion, wherein a balloon is attached at its proximal end to the outer surface of said middle portion and at its distal end to said distal portion;

and wherein at least part of the conduit of said distal portion is constructed such that following radial expansion of the balloon to a first expanded state, said distal portion conduit is capable of responding to further expansion of the balloon to a second expanded state by reducing its inner diameter thereby being able to grasp a guidewire placed within the lumen of said distal conduit portion, thereby preventing movement of said guidewire relative to said inner shaft, and such that said middle portion inner conduit is capable of responding to further expansion of the balloon from said second expanded state to a third expanded state by increasing its length from a resting value, and of responding to subsequent partial deflation back to said second expanded state by reducing its length back to said resting value.

In the case of both of the bitumen implementations described immediately hereinabove, the inner conduit preferably comprises at least one portion constructed of at least two different shaped elastically deformable segments, each of said segments responding to different fluid pressures.

In one particularly preferred embodiment, the at least two elastically deformable portions comprise various blends of nylon and/or Pebax.

BRIEF DESCRIPTION OF THE DRAWINGS

The present invention is illustrated by way of example in the accompanying drawings, in which similar references consistently indicate similar elements and in which:

FIG. 4 schematically illustrates various distal tip implementations that may be used in the balloon catheter of the invention;

FIGS. 5A and 5B schematically illustrates alternative balloon configurations that may be used in the balloon catheter of the invention;

FIG. 6 schematically illustrates an implementation of the balloon catheter of the invention wherein an auxiliary tube is used instead of the inner guide wire tube;

FIGS. 9A to 9C illustrate three different embodiments of the balloon catheter of the present invention using a bi-lumen conduit instead of a concentric inner tube-outer tube configuration proximal to the balloon attachment;

DETAILED DESCRIPTION OF PREFERRED EMBODIMENTS

Figure 1:
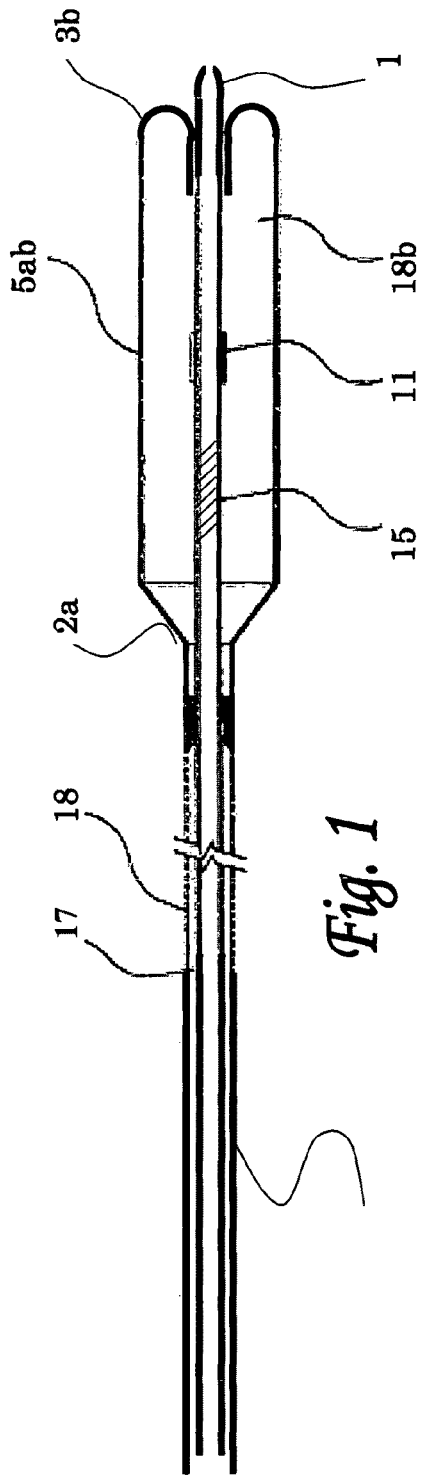
FIG. 1 schematically illustrates an over the wire implementation of the balloon catheter of the invention.

The present invention provides devices and methods for the treatment of vascular occlusions by means of disrupting vascular occlusions (particularly in cases of CTO) or other blockages formed within blood vessels in order to provide pathways for the placement of interventional devices and catheters as part of an overall effort to restore normal circulatory function. In general terms, the catheter device of the present invention achieves its objectives by creating a path with the least possible mechanical resistance through or around the occlusion. Thus, the presently disclosed device includes a distally-advanceable inner shaft tip which is caused to rapidly move back and forth (i.e. distally and proximally), thereby "ramming" the lesion. In another embodiment, the rapid oscillation of the inner shaft tip is translated into rapid oscillation of a guide wire that is firmly held within the distal portion of the inner shaft lumen, and which projects beyond the distal ending thereof. In addition, the devices comprise an inflatable balloon for anchoring the catheter inside the vessel.

In one preferred mode of operation, the device of the present invention creates the aforementioned path of least resistance by means of mechanically fracturing the vascular occlusion, while at the same time, greatly minimizing the risk of perforating the endothelia of the vascular wall. The latter advantage is achieved, in part, by virtue of the fact that the distal tip of the inner catheter shaft (and, in certain embodiments the distal tip of the guide wire) actually moves a very short distance (distally and proximally), thereby reducing the possibility that said tip will deviate from its centered position and motion.

In another aspect of the invention, following disruption of the occluding lesion, the pathway thereby created through said lesion is used to accommodate the conventional angioplasty balloon feature of the catheter, in order to simultaneously treat the vessel using conventional balloon angioplasty methods as part of an overall effort to restore normal circulatory function within the blood vessel.

In its most general form, the crossing balloon system disclosed and described herein comprises a novel balloon catheter, the fluid pressure inside of which may be rapidly increased and decreased by means of a pressure generator console connected thereto.

The balloon catheter of the present invention comprises a flexible inner catheter shaft fitted within a rigid outer shaft. The distal portion of the catheter defines an inflation lumen, as will be described in more detail hereinbelow. A balloon is connected at its proximal end to the distal end of the outer shaft section and at its distal end to the inner shaft, and is in fluid communication with the inflation lumen.

The manner in which the distal tapered extremity of the balloon is affixed to the distal end of the flexible inner catheter shaft permits the distal end of said balloon to roll and expand in response to increased pressure inside the catheter system. Similarly, as a result of this pressure increase, the inner shaft is caused to be stretched distally. Subsequently, when the pressure inside the catheter system is reduced, the elasticity of the inner shaft causes retraction (i.e. in a proximal direction) of the inner shaft tip to its original position in response to decreased pressure. In one main embodiment of the device of the present invention, a rapid, reciprocating pressure cycle (having a frequency in the sonic or subsonic range) thus causes a correspondingly rapid linear oscillatory motion of the distal tip of the inner catheter shaft. In this way, the rapid cyclical distal-proximal movement of the inner shaft tip, together with the shock waves set up within the volume of blood situated between the inner shaft tip and the obstruction, may be used to progressively cut through an intravascular lesion located in the region of the inner shaft tip. In a second main embodiment of the invention, to be described in more detail hereinbelow, the device further comprises means for firmly grasping a guide wire within the inner catheter shaft, such that the oscillating protruding distal tip of said guide wire is used to cut through the obstructing lesion.

In the case of both of these main embodiments, as mentioned hereinabove, the ability of the distal end of the balloon to roll and expand in response to increased pressure inside the catheter system is determined by the manner in which said distal end is affixed to the inner shaft. Essentially, the distal end of the balloon needs to be attached to the inner shaft in such a way that, during the part of the method of use wherein said balloon is caused to oscillate, said distal end is intussuscepted. This may be achieved in two different ways:

I. Pre-charged balloon conformation
In this conformation, the balloon is attached to the distal end of the inner shaft during manufacture such that its distal end is always intussuscepted (i.e. inwardly-folded onto the catheter shaft. This conformation may be achieved in a number of different ways as will be discussed further hereinbelow.

II. Non-charged balloon conformation
In this conformation, the distal end of the balloon is attached to the inner shaft of the catheter in a conventional, non-intussuscepted manner. The distal intussusception is then created by the operator by means of moving the inner shaft in a proximal direction (in relation to the outer shaft). The inner shaft is then locked in place, thereby preserving the distal intussusception created by this procedure.

The balloon catheter of the present invention may be constructed as an over-the-wire catheter or as a single-operator (i.e. rapid exchange) catheter. In addition, the catheter may also be manufactured using bi-lumen catheter tubing (for at least a portion of the total length of the catheter), as will be described hereinbelow.

In a preferred embodiment, the aforementioned balloon catheter is manufactured as a sterile, single use catheter, which is entirely disposable.

The balloon catheter is, as mentioned hereinabove, connected to a reusable pressure generator console, wherein said console comprises a pressure pump, a pressure adjustment interface and a display providing control information for the physician. In one embodiment, the pressure generator console includes a piston and a chamber with an actuation member attached to the piston. The chamber may be used to introduce inflation fluid (e.g. contrast material or saline solution) into the pressure generator and the inflation lumen. A pressure sensor/gauge and a balloon sizing scale may be incorporated into the catheter assembly to assist the treating physician in monitoring the procedure. A longitudinally oscillating drive, such as a solenoid and/or a rotary electrical motor, may be operatively connected to the pressure generator.

The procedure begins by advancing a guidewire within a blood vessel to a vascular occlusion. The catheter is advanced over the guidewire so that the distal end of the catheter is in proximity to the vascular occlusion. The guidewire is slightly retracted from the catheter tip. The balloon, the distal tip of which is located just proximal to the lesion to be treated, is then inflated to a first inflation pressure (anchoring pressure) which causes the balloon to be anchored within the confines of the blood vessel. Preferably, a symmetrical balloon inflation shape is used in order to ensure that the tip of the catheter is centered within the vessel in front of the occlusion. In non-charged versions of the device, the physician can manipulate the inflated balloon by releasing a grasping element that allows the inner shaft to be moved relative to outer shaft. The inner shaft is then retracted proximally and anchored at its new location by re-applying the grasping element. Proximal retraction of inner shaft folds the distal end of balloon inwardly and shortens the balloon's length (i.e. causes intussusception). If required, the operator may then advance the balloon catheter device distally in order to diminish the distance between distal tip and the occlusion. This is preferably carried out by partially deflating the balloon, thereby releasing its anchor in vessel, and advancing the device distally until the catheter's tip contacts the occlusion.

After re-anchoring the balloon in its new position at the treatment site, the user may operate the device in a vibrating mode by applying an oscillating pressure source to open a passage through the occlusion. During the phase of the oscillatory cycle wherein the balloon-pressure is increased from the anchoring pressure to a higher pressure, the elastic inner shaft extends and allows the distal balloon taper to roll and advance the catheter inner shaft tip in a forwards (i.e. distal) direction. Subsequently, during the phase of the oscillatory cycle wherein the balloon pressure is reduced back to the anchoring pressure, the elastic properties of the inner shaft will cause said shaft to move in a reverse (i.e. proximal) direction. This rapid, cyclical increase and decrease in fluid pressure that is produced by the pressure generator console thus results in a rapid distal-proximal linear motion of the inner shaft tip. This motion takes place over only a very short distance in order to keep the inner shaft tip centered within the vessel lumen. After the lesion in front of the catheter has been treated (i.e. rammed, scored and/or fractured by the vibrating inner shaft tip and/or distal tip of a guide wire immobilized within said vibrating shaft), the balloon is deflated, advanced further distally through the lesion and the procedure is then repeated, thereby traumatizing the next portion of the lesion. Once the operator has succeeded in crossing the lesion with the guidewire the catheter system may then be further used to dilate the lesion and create a passage for a stent or a larger diameter balloon dilatation catheter, using conventional angioplastic techniques that are well known in the art.

The method of the present invention may be used as the primary or sole means for crossing a CTO lesion. Alternatively, it may be employed after an unsuccessful attempt to cross the lesion using a conventional guidewire or cutting tool method.

Several preferred embodiments of the device of the present invention will now be described in more detail, with reference to the accompanying drawings. It will, of course, be understood that the particular embodiments described herein are brought for the purpose of illustration only, and that the scope of the present invention is not limited to these specific embodiments alone. The first group of implementations to be described (with reference to FIGS. 1 to 9) relate to the first of the two main embodiments described hereinabove, that is, the embodiment wherein the vibrating distal tip of the catheter inner shaft is used to traumatize the occluding plaques. Following the description of this first group of implementations, the second main embodiment (i.e. devices having a guide wire immobilized within the inner catheter lumen) will then be described in detail.

First Main Embodiment

Balloon Catheter Having Oscillating Catheter Shaft Distal Tip

FIG. 1 schematically illustrates an over the wire implementation of the balloon catheter of the invention. This balloon catheter implementation comprises an outer shaft 18, inner shaft 17 passing thereinside, and a balloon 5ab. The lumen of inner shaft 17 may be used for passing a guide wire thereinside, which may be introduced via its proximal opening (e.g., 12 in FIGS. 7A-7F). In the pre-charged embodiment shown in this figure, balloon 5ab has a conical proximal end 2a which tapers proximally towards its annular attachment area on the outer surface of the distal end portion of outer shaft 18, and a rounded distal end 3b which is obtained by folding the distal end of balloon 5ab proximally inwardly and by attaching the outer surface of its distal end portion to an annular attachment area on the outer surface of the distal end portion of inner shaft 17. Other types of balloon attachment (resulting in either pre-charged or non-charged balloons) are also possible, one example of which is described in more detail hereinbelow.

Inner shaft 17 is manufactured either from an elastic material or from an essentially non-elastic material that incorporates at least one elastic portion 15 along its length. Of course elastic portions 15 may be obtained in many various ways, as will be exemplified hereinafter with reference to FIG. 3. Inner shaft 17 may further comprise a radiopaque marker 11. The distal tip 1 of inner shaft 17 is preferably made rigid to allow using it for opening a passage via an occluded vessel. Inflation fluid lumen 18a (shown in FIG. 2) obtained between the inner shaft 17 and the inner wall of outer shaft 18 provides a path for filling the inner space 18b of balloon 5ab with pressurized inflation fluid provided therethrough.

In a typical procedure the balloon catheter is inserted and advanced through the patient's vessels in a deflated state towards a treatment site which may comprise an occlusion. After reaching the treatment site inflation fluids are pressurized via inflation fluid lumen 18a and fill inner space 18b of balloon 5ab. The wall of the inflated balloon is pressed against the inner wall of the blood vessel, thereby anchoring it at the treatment site. In the case of a catheter utilizing a non-charged balloon (e.g. the balloon depicted in FIG. 5A), in order to operate said catheter in its vibrating mode the inner shaft 17 is slightly retracted proximally (e.g., about 3 mm) and affixed in its displaced location. Proximal retraction of inner shaft 17 cause distal end portion 3b of balloon 5ab to collapse proximally inwardly on the outer surface of distal end portion of inner shaft 17, thereby shortening the balloon's length and reducing its volume. Portions of the inflation fluid may be discharged via inflation fluid lumen 18a into an inflation fluid reservoir (not shown) in order to prevent substantial pressure increase therein.

The distal end of inner shaft 17 may then be vibrated about its longitudinal axis by applying an oscillatory pressure source for periodically changing the pressure of the inflation fluid in balloon 5ab. Such periodical pressure changes cause corresponding lengthening and shortening of the lengths of balloon 5ab and inner shaft 17, thereby traumatizing and/or rupturing the occlusion and thereby opening a passage therethrough.

In the case of a catheter deploying a pre-charged balloon (e.g. the balloon depicted in FIG. 1), the procedure for using the catheter in a crossing procedure is essentially the same as described hereinabove, except for the fact that the inner shaft need not be withdrawn proximally prior to causing the distal-proximal oscillation of the balloon.

Outer shaft 18 may be manufactured by an extrusion and laser cutting process from a polymer, composite or metallic material, such as stainless 316, Nitinol, or nylon, its longitudinal length is generally in the range of 100 to 2000 mm, preferably about 1200 mm, and its diameter is generally in the range of 1 to 2 mm, preferably about 1.2 mm. Inner shaft 17 may be manufactured by an extrusion and laser cutting process from a flexible polymer, composite materials or metallic material, such as pevax, nylon, stainless steel or nitinol, its longitudinal length is generally in the range of 100 to 2000 mm, preferably about 1200 mm, and its diameter is generally in the range of 0.3 to 1 mm, preferably about 0.8 mm. Elastic portions 15 may be obtained by combining one of the above mentioned materials, preferably elastomers, in such portions. A particularly preferred material comprises a blend of nylon and Pebax, for example Pebax 5333, Pebax 6333 and so on.

The distal tip 1 of inner shaft 17 may be stiffened by combining stiffening materials such as composite or metals materials therein, and it is preferably has a sharp end for improved penetration. Additionally or alternatively, distal tip 1 may be stiffened by making it thicker relative to other portions of inner shaft 17.

Figure 2:
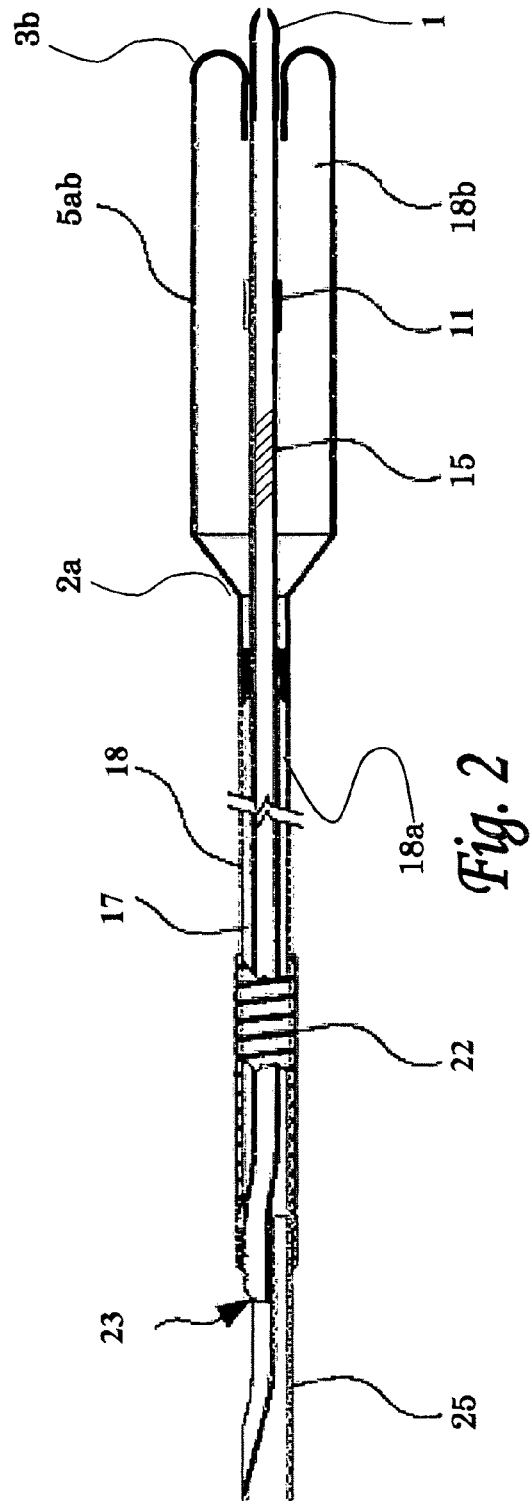
FIG. 2 schematically illustrates a rapid exchange implementation of the balloon catheter of the invention.

FIG. 2 schematically illustrates a rapid exchange implementation of the balloon catheter of the invention. The vibration mechanism in this rapid exchange balloon catheter implementation is substantially similar to the mechanism described above with reference to FIG. 1. The catheter's structure mainly differs in that the lumen of its inner shaft may be accessed via a lateral port 23 provided between the proximal and distal ends of the catheter. Inflation fluid lumen 18a in outer shaft 18 may be filled with pressurized inflation fluids via proximal tube 25 attached thereto. Strain relief portion(s) 22 may be provided over the outer surface of outer shaft 18 for providing additional transitional support and reducing the potential collapse of the catheter's tubes/shafts.

The longitudinal length of inner shaft 17 is generally in the range of 100 to 300 mm, preferably about 120 mm. Proximal tube 25 is made from a flexible polymer, composite or metallic material, such as pevax, nylon, stainless steel or nitinol, having a longitudinal length generally in the range of 100 to 1700 mm, preferably about 1000 mm, and it may be attached to outer shaft 18 by strain relief portion(s) 22 that can be structured by means of over extruded section or heat shrink tube section.

Figure 3:
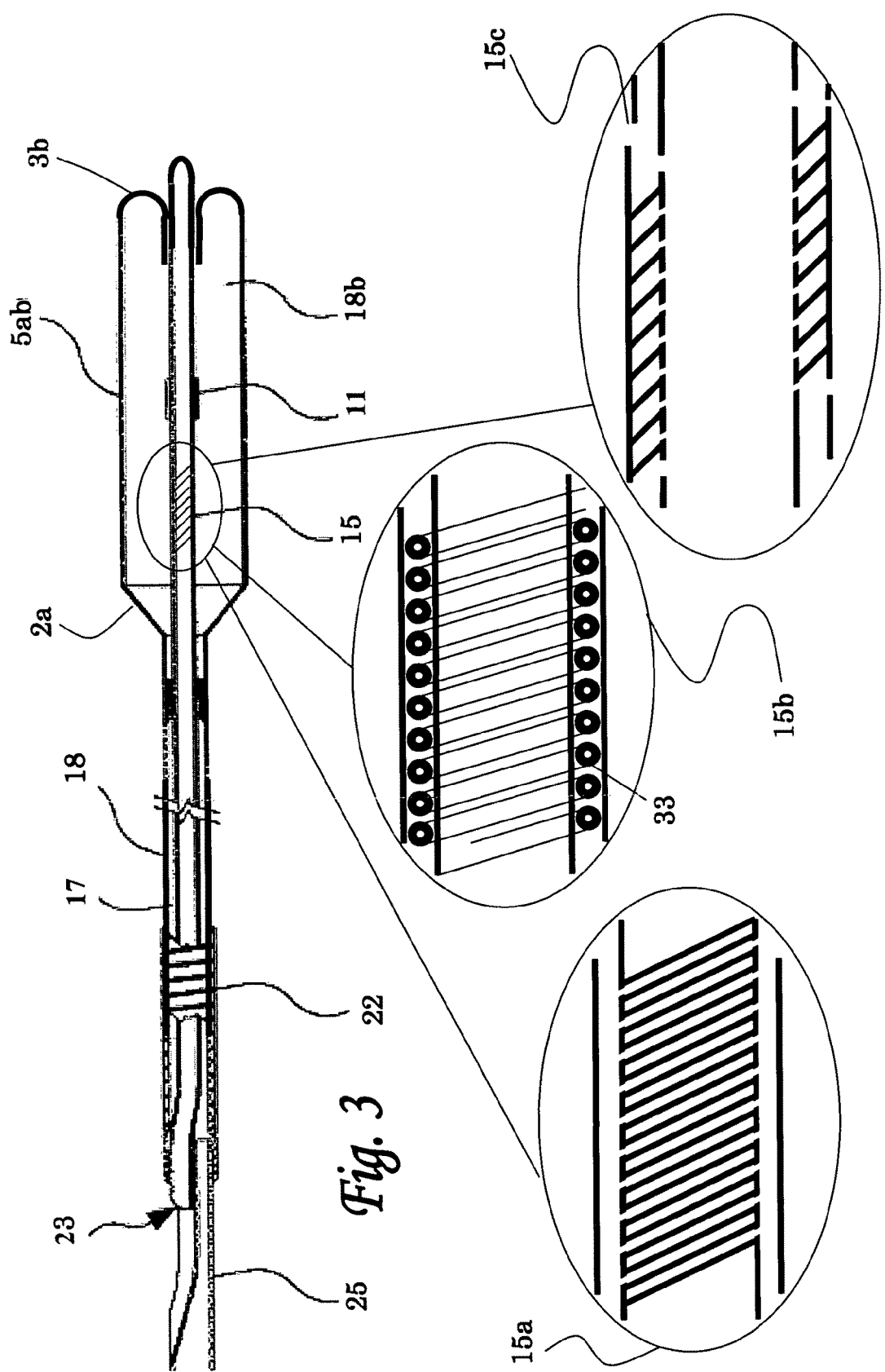
FIG. 3 demonstrates various elastic shaft implementations according to preferred embodiments of the invention.

FIG. 3 demonstrates various elastic inner shaft portion implementations that may be used in the balloon catheter of the invention. Elastic portion 15 may be constructed by combining a braided coil section 15a with an intermediate section thereof. Braided coil, such as manufactured by coil winding processes, may be manufactured from a composite material or as an inner coil with over extrusion of Polymers/elastomers type of materials. The length of the braided coil 15a combined in inner shaft 17 is generally in range of 3 to 15 mm, preferably about 10 mm.

In and alternative implementation elastic portion 15b is obtained by embedding coil 33 in an intermediate section thereof. Coil 33 may be embedded in the wall of a portion of inner shaft 17, or on its outer or inner surface. Coil 33, such as manufactured by coil winding techniques, may be manufactured from a metallic material and it may be adhered to inner shaft 17 using an acrylic type of adhesive, or embedded in its wall via an over extrusion process. The length of coil 33 is generally in range of 3 to 15 mm, preferably about 10 mm.

Additionally or alternatively, elastic portions 15c made from one or more elastic material, such as elastomers, polymers, or composite materials, may be embedded in intermediate sections of inner shaft 17. Elastic portions 15c may be adhered in intermediate portions of inner shaft 17 using an acrylic, epoxy, or vulcanized type of adhesive, or attached therebetween using an ultrasonic/thermal bonding welding process. The length of elastic portion 15c is generally in range of 3 to 15 mm, preferably about 10 mm.

FIG. 4 schematically illustrates various distal tip 1 implementations that may be used in the balloon catheter of the invention. Distal tip 1 may be shaped in various forms for achieving a desired rupture effect. A connector (not shown) may be provided at the distal end of the catheter for allowing the physician to choose a suitable tip 1 and connect it thereto. The tip may have a sharp shape as demonstrated in tip 1a, a blunt shape as demonstrated in tips 1b and 1c, or a drill like shape as in tips 1d and 1e. Tip 1, such as manufactured by machining, may be manufactured from a metal or composite type of material and its length is generally in range of 1 to 5 mm, preferably about 2 mm.

FIGS. 5A and 5B schematically illustrate alternative balloon configurations that may be used in the balloon catheter of the invention. FIG. 5A demonstrates a non-charged implementation of the balloon catheter of the invention wherein both proximal and distal ends, 2a and 3a, of balloon 5aa have conical shapes. The shape of balloon 5aa is obtained by using a balloon having tapering ends the inner surfaces of which are attached to the outer surfaces of end portions of outer shaft 18 and inner shaft 17. In the pre-charged example shown in FIG. 5b both proximal and distal portions, 2b and 3b, of balloon 5bb have a rounded, intussuscepted shape which is obtained by attaching the outer surface of the end portions of balloon 5bb to the outer surface of end portions of outer shaft 18 and of inner shaft 17. Typically, in order to attach the outer surfaces of the end portions of balloon 5bb in this way, its distal end 3b is folded proximally inwardly and its proximal end 2b is folded distally inwardly.

Balloon 5 may be a non-compliant or semi-compliant or low-compliant balloon, such as manufactured by Interface Assoc, may be manufactured by conventional methods known in the balloon catheter industry from a biocompatible polymer material, preferably from nylon 12 or PET (polyethylene terephthalate). The angle of conical ends of balloon 5, such as in balloons 5ab and 5aa, is generally in range of 10° to 90°, preferably about 40°.

FIG. 6 schematically illustrates an alternative implementation of the balloon catheter of the invention wherein an auxiliary tube 50, laterally attached to the outer surface of an end section of outer shaft 18, is used as a guide wire lumen instead of inner shaft (17). Auxiliary tube 50 has proximal and distal openings for passing a guide wire therethrough. In this way the balloon catheter of the invention may be manufactured with a single lumen employing the hollow interior of shaft 18 as an inflation fluid lumen. The distal end section of the catheter comprising balloon 5 comprises an inner shaft 67 which proximal end is attached at one or more attachment points 62 located between the proximal ends of balloon 5 and of the catheter to the inner wall of outer shaft 18. Inner shaft 67 comprises one or more elastic portions 15, a radiopaque marker 11, and a tip 1g adapted for rupturing an occlusion. Auxiliary tube 50 may be manufactured from a flexible polymer or metal and it may be adhered to the outer surface of outer shaft 18 using adhesives or ultrasonic welding/thermal bonding, and its length is generally in range of 100 to 300 mm, preferably about 120 mm.

FIGS. 7A to 7F demonstrate one possible procedure for opening a path through an occluded vessel 20 using the balloon catheter of the invention 10. In this example a non-charged balloon 5aa is used which has proximal and distal tapering ends attached to the outer surface of a distal portion of outer shaft 18 and of inner shaft 17, at attachment points 7 and 6, respectively. Catheter 10 may be advanced towards the treatment site over guide wire 13 threaded through the lumen of inner shaft 17. Catheter 10 should be placed as near as possible to occlusion 70, preferably such that distal tip 1 contacts said occlusion. Once catheter 10 is placed in the treatment site balloon 5aa may be inflated to a first, anchoring diameter by introducing pressurized inflation fluids (designated by arrows 8a) via inflation fluid port 11. Inflation fluids pass via inflation fluid lumen defined between inner wall of outer shaft 18 and the outer surface of inner shaft 17. In its inflated state (FIG. 7B) lateral sides of balloon 5aa are pressed against the inner wall 21 of vessel 20, thereby anchoring it thereto.

After anchoring the balloon in the treatment site the operator manipulates the inflated balloon by releasing a grasping element 14, thus allowing inner shaft 17 to be moved proximally relative to outer shaft 18. Inner shaft 17 is retracted proximally and locked into its new location by re-applying grasping element 14 (FIG. 7C). Graduated scale 19, provided on a proximal portion of inner shaft 17, may be used to assist the operator in determining the length of inner shaft 17 which has been retracted. Proximal retraction of inner shaft folds the distal end of balloon 5aa proximally inwardly and shortens the balloon's length and consequently reduces its inflated volume as portions of inflation fluid are discharged therefrom (designated by arrows 8b).

The discharged portions of inflation fluid may be received by an inflation fluid reservoir (not shown) via inflation fluid port 11 or via a dedicated discharge outlet (not shown). Alternatively or additionally, the pressure changes in the device may be absorbed utilizing mechanical or pneumatic means (not shown). For example, a gas (e.g., air) bubble (e.g., balloon filled with air) may be placed in outer shaft 18, which will absorb volumetric changes and thus prevent substantial pressure changes in the shaft 18. As another example, volumetric changes in shaft 18 may be absorbed by using a movable piston mechanism which can restore a non-pressed state via a spring attached thereto.

The operator may advance the balloon catheter device distally in order to diminish the distance between distal tip 1 and occlusion 70, if required. This is preferably carried out by partially deflating balloon 5aa, thereby releasing its anchor in vessel 20, and advancing the device distally until tip 1 contacts occlusion 70.

Figure 7A:
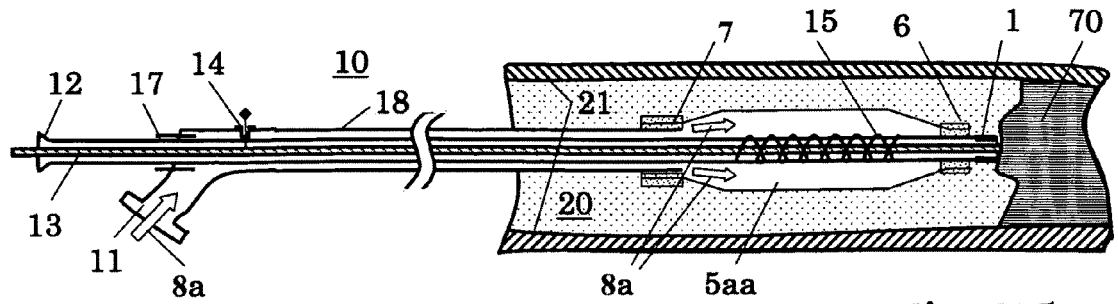
FIGS. 7A to 7F demonstrate one possible procedure for opening a path through an occluded vessel.
Figure 7B:
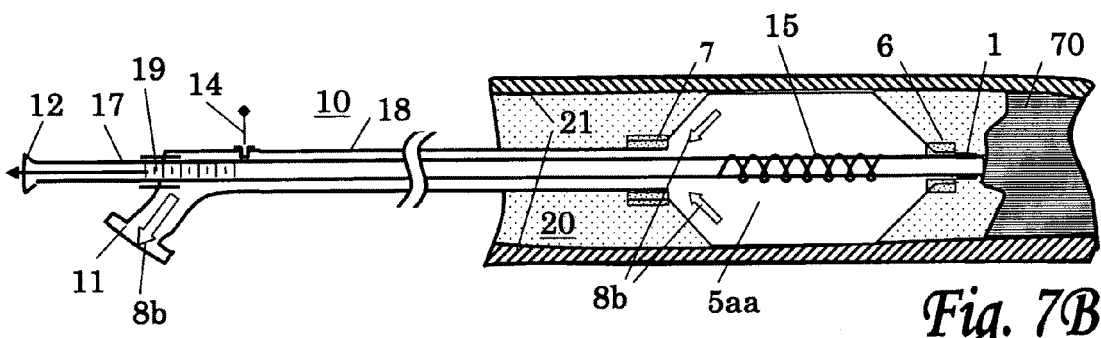
Figure 7C:
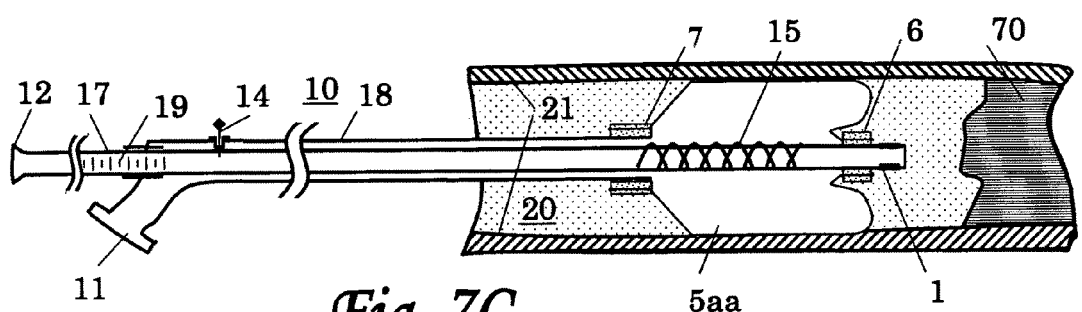
Figure 7D:
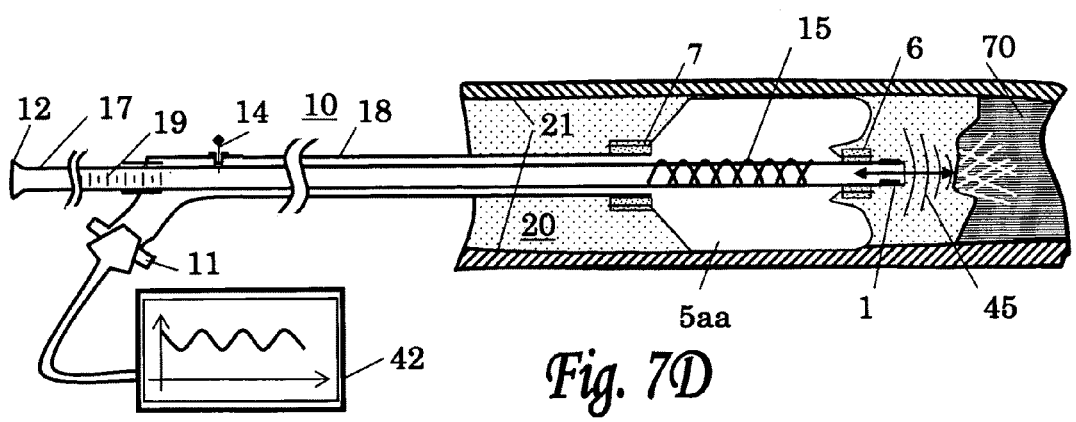

FIG. 7D demonstrates operation of the balloon catheter 10 in a vibrating mode by applying an oscillating pressure source 42 via inflation fluid port 11, which generates periodical pressure changes in balloon 5aa. These periodical pressure changes result in periodical lengthening and shortening of balloon 5aa and elastic portion 15 of inner shaft 17. The vibrating movement of distal tip 1, and/or the shockwaves 45 established thereby, fracture occlusion 70 and open a pathway therethrough.

Figure 7E:
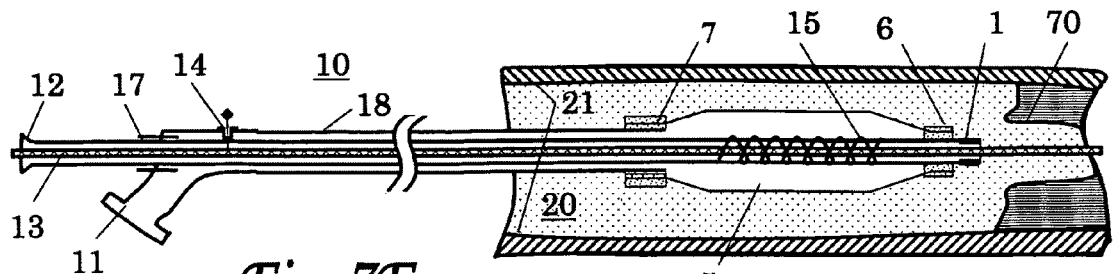
Figure 7F:
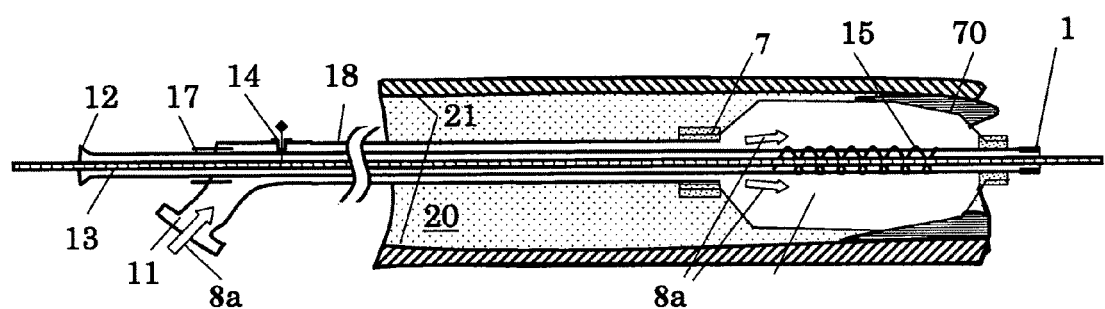

As shown in FIG. 7E guide wire 13 may be then advanced into the fractured occlusion and thereafter the balloon catheter may be also advanced thereinto after deflating balloon 5aa. At this state the fractured occlusion may be dilated by inflating balloon 5aa as shown in FIG. 7F.

In the case of a pre-charged balloon catheter, the procedure is essentially the same as described above, except that the step of withdrawing the inner shaft proximally (in order to create an intussusception at the distal end of the balloon) as shown in FIG. 7B, is omitted.

The pressure in balloon 5aa in its inflated state is generally in the range of 2 to 10 atmospheres, preferably about 4 atmospheres, and in its folded state in the range of 2 to 10 atmospheres, preferably about 5 atmospheres. Oscillatory pressure source 42 may be implemented in various ways, for example, by utilizing a peristaltic or diaphragm pump, and the pressure oscillations may be controlled by utilizing a solenoid or a revolving eccenter, for instance.

The pressure of the inflation fluid in balloon 5 may be measured by a pressure gauge (not shown) installed at a suitable location along the inflation path, such as in the inflation fluid lumen, for example. Alternatively, the inflation fluid pressure may be obtained utilizing an expansion based indicator (e.g., a flexible part which reacts to pressure by elongating) or by mechanical displacement indicator (e.g., indicator which records the longitudinal movement of the cylinder and translates it to pressure changes).

In one embodiment, balloon 5 may be attached to the catheter in such a way that said balloon is twisted along its longitudinal length. Such a longitudinal twist may be obtained by slightly rotating attaching one of the balloon's ends and attaching it to its respective attachment point. In this way the inflation of balloon 5 will apply a rotational force on the inner shaft 17 attached thereto which cause elastic portions 15 thereof to twist and thus provide a drilling effect by slightly rotating tip 1 about its axis. It should be noted that a similar effect is also obtained when using spring like elements to implement elastic portions 15 due to the twist induced by such elements during stretch and compression thereof.

Figure 8A:
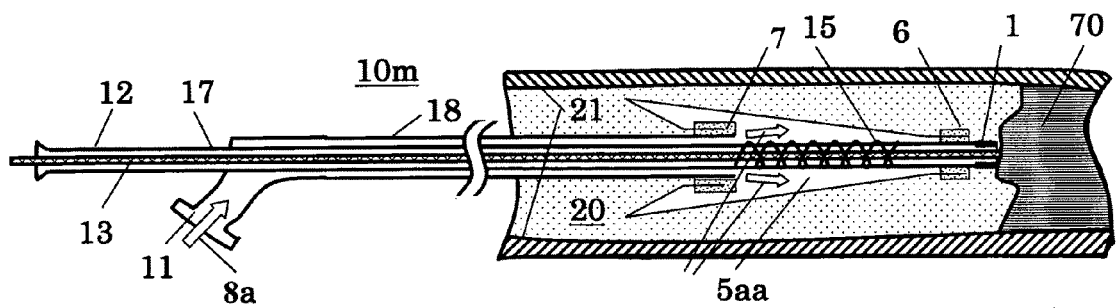
FIGS. 8A and 8B demonstrate another possible procedure for opening a path through an occluded vessel.
Figure 8B:
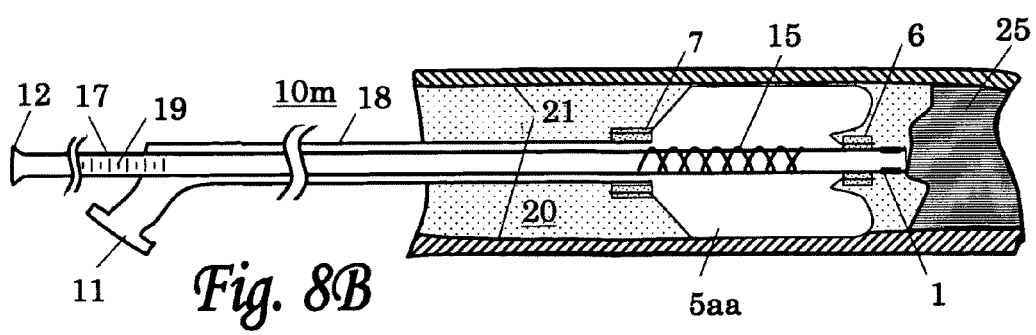

Another example for a procedure for opening a path through an occluded vessel 20 that may be performed with a modified balloon catheter 10m of the invention will be now described with reference to FIGS. 8A and 8B. In this example inner shaft 17 is affixed to outer shaft 18 (e.g., using a suitable adhesive), and balloon 5aa is folded proximally (backwardly) thus forming an arrow-like shape which tapers towards its distal attachment point 6, as shown in FIG. 8A. This folded state may be retained by folding the balloon into this folded state under heat and/or pressure (e.g., while folding the balloon in the manufacturing process the balloon will maintain its shape if the "wings" of the folded jacket will remain tight).

Catheter 10m may be advanced towards the treatment site over guide wire 13 threaded through the lumen of inner shaft 17. Catheter 10m is placed adjacent to occlusion 70, preferably such that distal tip 1 contacts said occlusion. Once catheter 10m is placed in the treatment site balloon 5aa may be inflated by introducing pressurized inflation fluids (designated by arrows 8a) via inflation fluid port 11. Inflation fluids pass via inflation fluid lumen defined between inner wall of outer shaft 18 and the outer surface of inner shaft 17. In its inflated state (FIG. 7B) lateral sides of the backwardly folded balloon 5aa are pressed against the inner wall 21 of vessel 20, thereby anchoring it thereto. Due to its initial folded state the distal end of the inflated balloon gains a rounded, intussuscepted shape, as shown in FIG. 8B.

After anchoring the balloon in the treatment site the physician may operate the device in a vibrating mode by applying an oscillating pressure source 42 via inflation fluid port 11, open a passage through the occlusion and perform balloon dilatation in needed, as was previously described with reference to FIGS. 7D to 7F.

The pressure in balloon 5aa in its inflated state is generally in the range of 2 to 10 atmospheres, preferably about 4 atmospheres, and in its folded state in the range of 2 to 10 atmospheres, preferably about 5 atmospheres.

While in the figures an inner shaft 17 comprising an elastic portion is shown, it should be understood that the entire inner shaft may be manufactured from an elastic material.

It should be noted that balloon 5 may be operated also manually or mechanically in procedures such as described hereinabove. For example, the operator can carry out the occlusions opening steps (or portion thereof) of the procedure by pulling inner shaft 17 proximally and releasing. Such operation will cause proximal and distal movements of tip 1 and assist in rupturing occlusion 70. Similarly, mechanical means (not shown e.g., mechanical actuator which can be used on the proximal end of the catheter to reciprocatingly move withdraw the inner shaft and release against the flexibility of the balloon accumulating pressure change) may be used to introduce such movements of tip 1.

Figure 9A:
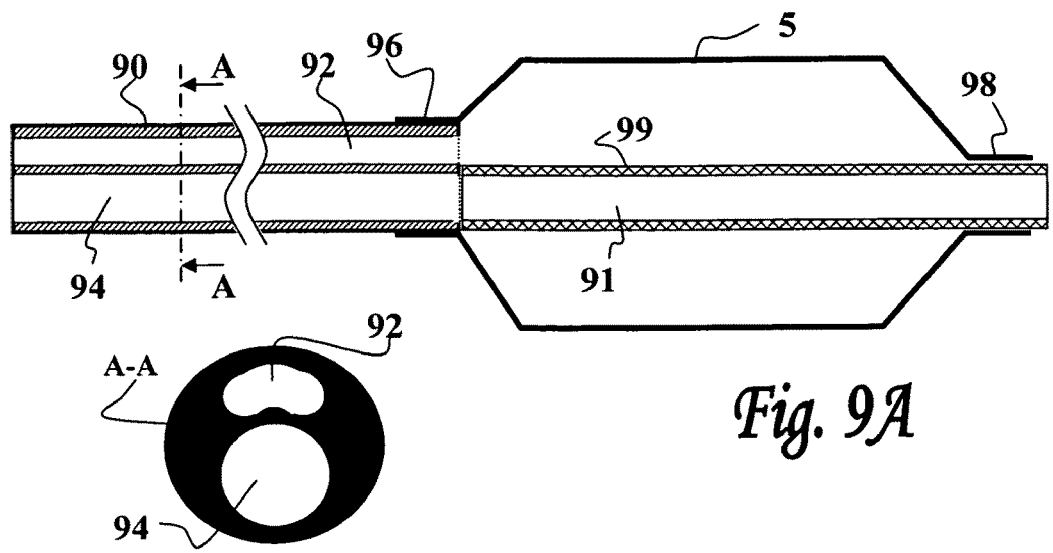

FIG. 9A illustrates one embodiment of the invention utilizing bitumen catheter tubing along at least a portion of the overall catheter length. In this figure, the proximal end of balloon 5 is attached to the external surface of bitumen conduit 90 at proximal attachment point 96, said bitumen conduit comprising two parallel lumens: inflation fluid lumen 92 and guidewire lumen 94. A cross-sectional view of the bi-lumen conduit taken at level A-A which shows the relative arrangement of the two lumens, is provided in the lower part of this figure. While inflation fluid lumen 92 ends at the proximal balloon attachment point 96, guidewire lumen 94 continues beyond the proximal attachment point 96 of balloon 5, said lumen becoming continuous with the guidewire lumen 91 of distal conduit 99. The outer surface of said distal conduit, which contains an elastically deformable region, provides a distal balloon attachment point 98.

Figure 9B:
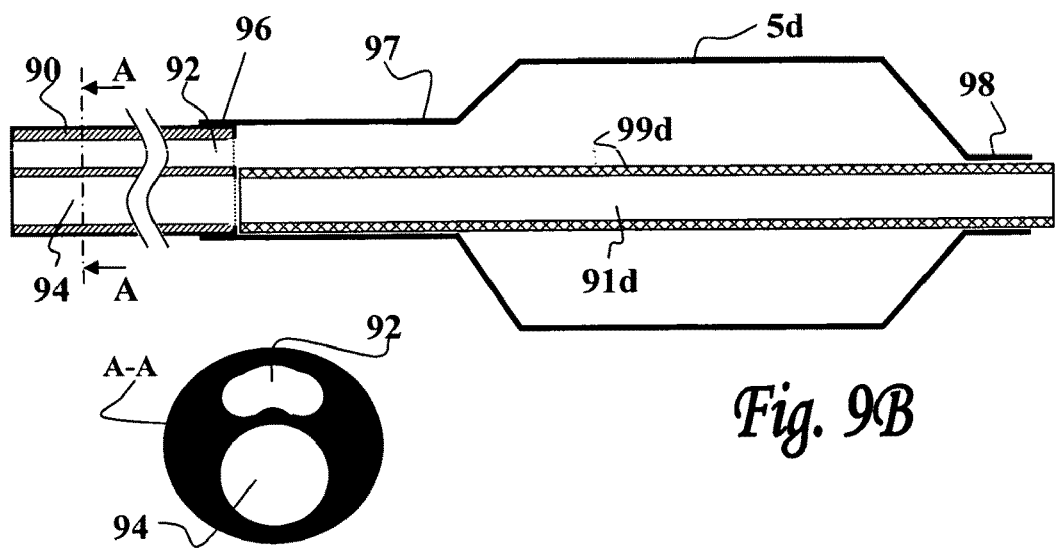

In certain circumstances, it is desirable to provide a bitumen catheter of the type described immediately hereinabove, in which the length of the elastically-deformable distal conduit is not limited by the length of the balloon. FIGS. 9B and 9C illustrate to further embodiments utilizing a bitumen conduit, in which this length restriction is removed.

Thus, in the embodiment of the catheter shown in FIG. 9B, the modified balloon, 5d, has an elongated proximal neck, 97. The increase in length of the balloon in this embodiment permits the use of a longer distal conduit 99d. All the other elements in this embodiment are the same as those shown in FIG. 9A.

FIG. 9C illustrates another embodiment of the bitumen configuration described hereinabove. In this case, the catheter further comprises a connecting tube segment 100 positioned between the conduit proximal portion (i.e. bitumen conduit) 90 and the proximal attachment point of the balloon 96. Said connecting tube segment, shown in cross-sectional view in the lower right portion of FIG. 9C, contains two concentrically arranged conduits: an outer conduit having a lumen 106 that is in fluid communication with the fluid passage lumen 92 of the proximal bitumen conduit 90, and an inner conduit formed by the elastic section-containing distal conduit 99d, the lumen 91d of which is in fluid communication with the guidewire lumen 94 of said bitumen conduit 90. As seen in the figure, the presence of connecting tube segment 100 permits the use of a longer distal conduit 99d than is possible in the embodiment depicted in FIG. 9A.

Figure 10A:
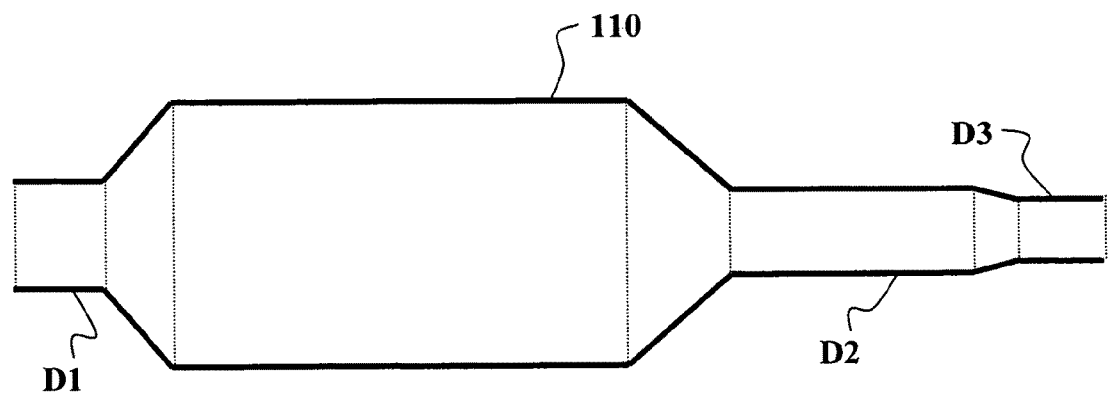
FIGS. 10A to 10E illustrate a method of producing a balloon catheter of the present invention having an intussuscepted distal balloon attachment.

As mentioned hereinabove, there exist several different procedures for attaching the balloon to the catheter shafts that may be employed in the manufacture of the devices of the present invention. One example of such a procedure, which is illustrated in FIGS. 10A to 10E, is known as 'flipped distal neck bonding'. As shown in FIG. 10A, the balloon 110 is blown from a length of standard tubing material (e.g. 0.6 mm diameter nylon 12 and/or a Pebax material).

Figure 10B:
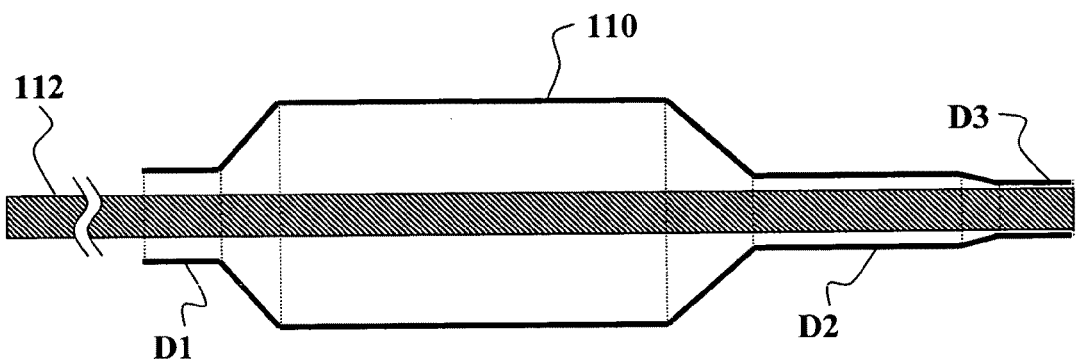
Figure 10C:
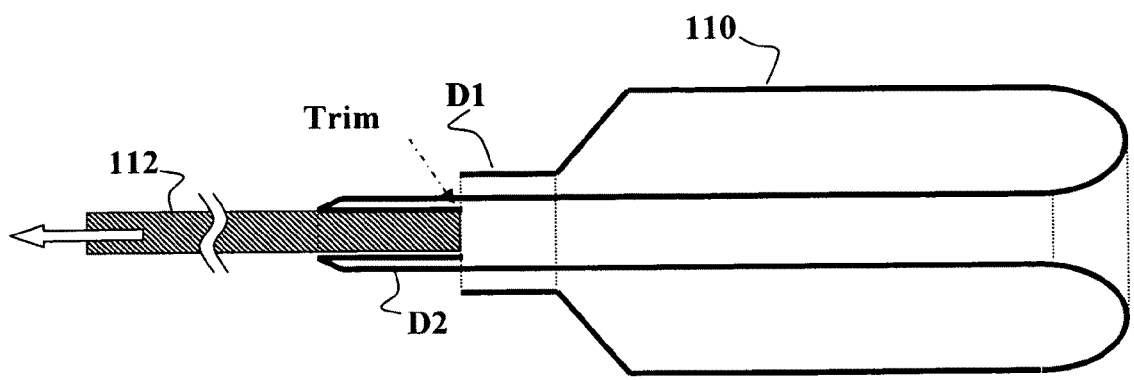
Figure 10D:
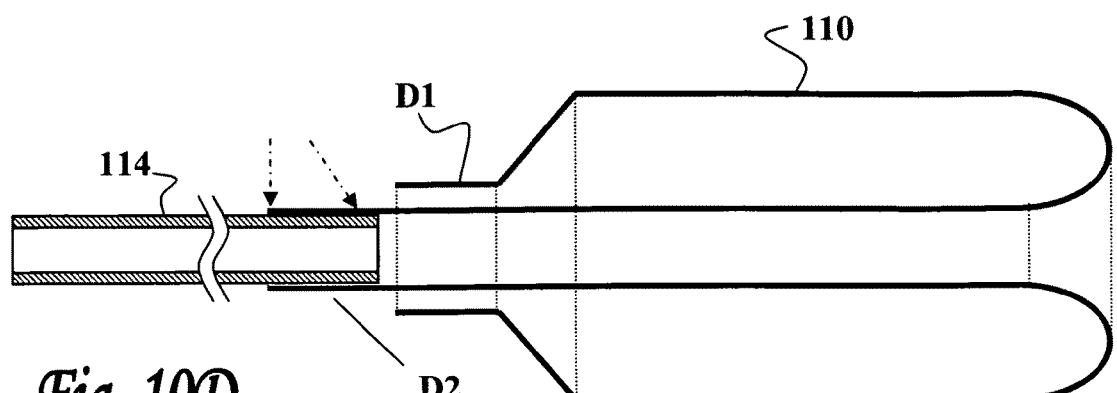
Figure 10E:
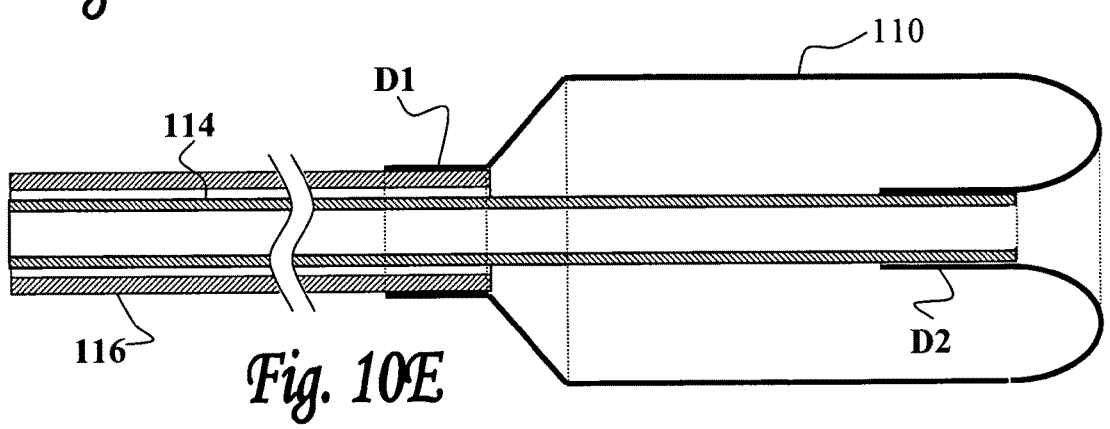

Following balloon blowing, the tubing that is continuous with the proximal and distal extremities of the balloon forms three distinct areas, each having different diameters. Thus, on the proximal side of the balloon, the tubing has inner diameter D1, said diameter matching the outer catheter shaft that is to be connected thereto. The region immediately distal to the balloon has diameter D2, said diameter matching the outer diameter of the inner catheter shaft. Finally, the distal-most region has a diameter D3 that is smaller than D2. The purpose of this undersized region, as shown in FIG. 10B, is to permit bonding to a mandrel 112 that is inserted through the lumen of balloon 110. The next stage, as shown in FIG. 10C is the pulling of mandrel 112 in a proximal direction (as shown by the arrow). Since the mandrel is firmly bonded to the distal-most portion of the balloon, the pulling motion results in inversion and intussusception of the distal portion of the balloon through its lumen. The mandrel is then trimmed at the point indicated by the arrow and removed. The next stage, as shown in FIG. 10D, is the insertion of the inner tube 114 into the portion of the tubing having diameter D2 that was originally located (e.g. in FIG. 10A) distal to the expanded portion of the balloon 110. The inner tube is bonded into inner tube 114 along the section of the tubing marked with arrows. FIG. 10E shows balloon 110 following the final stages of the procedure, wherein the balloon has been rolled back into its original position, and the outer tube 116 has been bonded into the distal neck of the balloon (the region having diameter D1). It may be seen from this figure that the balloon produced by this technique is pre-charged, having a distal intussusception.

Second Main Embodiment

Balloon Catheter Having Oscillating Guide Wire Immobilized within Catheter Shaft In this second main embodiment of the invention, the balloon catheter system comprises a guidewire (also referred to herein as a ramming tool) immobilized within an inner catheter shaft lumen, wherein the balloon catheter is capable of delivering rapid motion to the guidewire passing therein. The in vivo application of such rapid motion to, or adjacent to, an occlusion formed in a body organ or pathway is effectively utilized for fracturing the occluding matter and for perforating a passage thereinside, that may allow crossing and/or removing the occluding matter.

The balloon catheter of the invention is preferably constructed from concentric tubes having an inflatable member, such as a balloon, attached to their distal ends. The inflatable member can be a sleeve having tapering ends that can be sealably attached to the distal end portions of the inner and outer tubes of the catheter device, such that the lumen obtained between the inner and outer tubes can be used as an inflation lumen.

The balloon catheter device of the invention can be introduced into the body of the treated subject via an incision, and advanced therethrough over the guidewire to the treatment site, as carried out in conventional catheterization procedures. Radiopaque markers provided on the catheter device (and/or on the guidewire it is threaded on), or any other suitable visioning technique, may be used to guide the balloon catheter device to the treatment site. After reaching the treatment site the inflatable member is inflated with a suitable inflation fluid to anchor and center the catheter device thereinside, such that a volume of fluid (e.g., blood) is delimited by said inflatable member and the proximal face of said occluding matter.

The inflatable member preferably has an expandable distal end portion designed to distally expand in response to pressure increments provided therein, and the inner tube (or a portion thereof) is preferably made elastically deformable to allow distal elongation thereof. Repeated distal expansions of the inflatable member may be used to cause the inner tube to repeatedly stretch and retract axially in alternating (distal and proximal) directions. The inner tube of the balloon catheter is designed to grasp the guidewire passing in it prior to such oscillatory movements such that said movements of the inner tube are transferred to the guidewire which is advantageously used to fracture the occluding matter by repeatedly ramming into it.

Figure 11A:
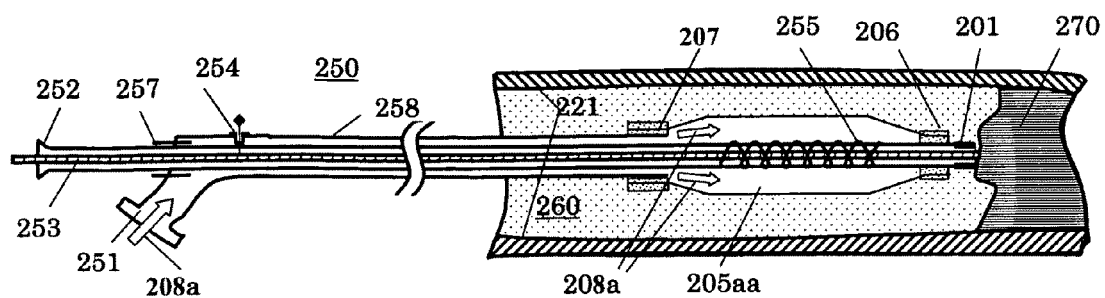
FIGS. 11A to 11C demonstrate one implementation of the second main embodiment of the invention and a procedure for catheter deployment at the occlusion site.
Figure 11B:
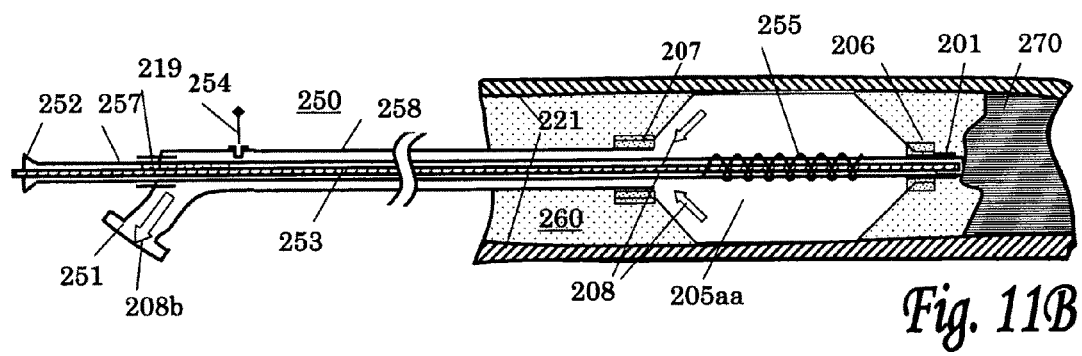
Figure 11C:
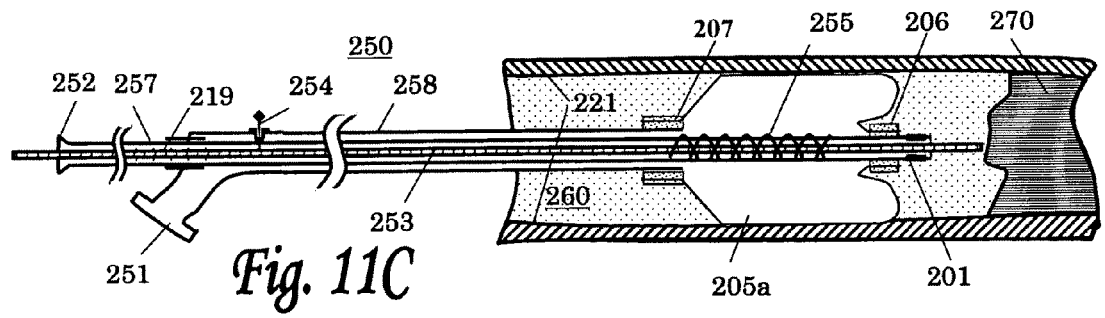

FIGS. 11A to 11C demonstrate one possible procedure for catheter deployment in front of the occlusion 270 using the balloon catheter of the invention 250. In this example balloon 205aa of balloon catheter 250 has proximal and distal tapering ends attached to the outer surface of a distal portion of outer shaft 258 and of inner shaft 257, at attachment points 207 and 206, respectively. Catheter 250 may be advanced towards the treatment site over guide wire 253 threaded through the lumen of inner shaft 257. Catheter 250 should be placed as near as possible to occlusion 270, preferably such that its distal tip 201 contacts said occlusion. Once catheter 250 is placed at the treatment site, balloon 205aa may be inflated to a first, anchoring pressure, by introducing pressurized inflation media (e.g., fluid, designated by arrows 208a) via inflation fluid port 251. The inflation media passes via inflation fluid lumen defined between inner wall of outer shaft 258 and the outer surface of inner shaft 257. In its inflated state (FIG. 11B) lateral sides of balloon 205aa are pressed against the inner wall 221 of vessel 260, thereby anchoring it thereto.

In the case of non-charged balloons (as defined and described hereinabove, in relation to the first main embodiment), following anchoring of the balloon at the treatment site the operator may manipulate the inflated balloon by releasing a grasping element 254 (immobilizer), thus allowing inner shaft 257 to be moved proximally relative to outer shaft 258. Inner shaft 257 is retracted proximally and anchored at its new location by restoring the grasp thereof by grasping element 254 (FIG. 11C). Graduated scale 219, provided on a proximal portion of inner shaft 257, may be used to assist the operator in determining the length of inner shaft 257 which has been retracted. Proximal retraction of inner shaft folds the distal end of balloon 205aa proximally inwardly and shortens the balloon's length and consequently reduces its inflated volume as portions of inflation fluid are discharged therefrom (designated by arrows 208b in FIG. 11B).

The discharged portions of inflation fluid may be received by an inflation fluid reservoir (not shown) via inflation fluid port 251 or via a dedicated discharge outlet (not shown).

At this point, distal end 201 of inner shaft 257 may be vibrated about its longitudinal axis by applying an oscillatory pressure source for periodically changing the pressure of the inflation media in balloon 205aa. Such periodical pressure changes cause corresponding lengthening and shortening of the lengths of balloon 205aa and elastic inner shaft 257 (or elastic portions thereof 255) which may be employed for rupturing the occlusion and thereby opening a passage pathway therethrough.

The operator may advance guidewire 253 such that distal end portions thereof may leave inner shaft 257 through its distal end opening, e.g., such that 1 to 5 mm of the wire protrudes from the distal end of the catheter, as demonstrated in FIG. 11C. This is preferably carried out by advancing proximal portions of guidewire 253 distally through proximal end opening 252 of inner shaft 257 such that a distal portion thereof protrudes outwardly via the proximal end opening (at distal tip 201) of inner shaft 257.

Figure 12A:
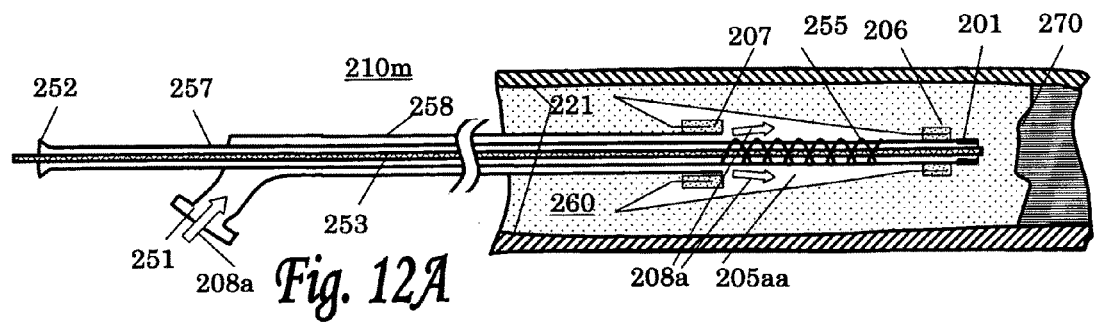
FIGS. 12A and 12B demonstrate another possible procedure for catheter deployment at the occlusion site.
Figure 12B:
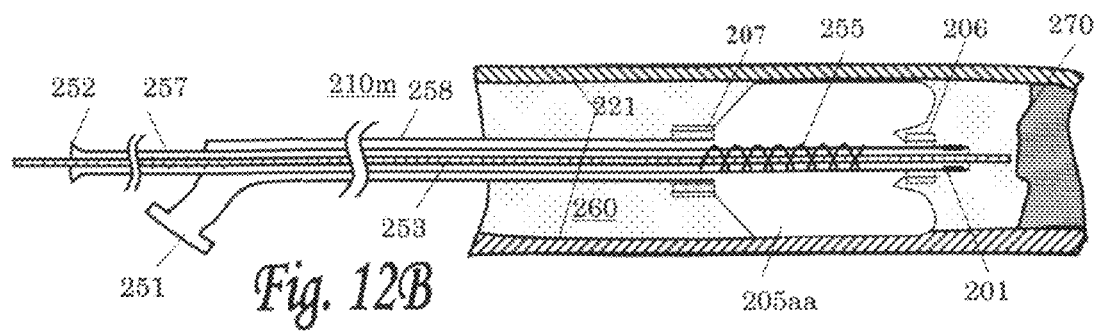

FIGS. 12A and 12B demonstrate another possible procedure for catheter deployment in front of the occlusion. In this example an alternative form of balloon catheter 210m is used, wherein inner shaft 257 is affixed to outer shaft 258 (e.g., using a suitable adhesive), and balloon 205aa is folded proximally (backwardly) thus forming an arrow-like shape which tapers towards its distal attachment point 206, as shown in FIG. 12A. This folded state may be retained by folding the balloon into this folded state under heat and/or pressure (e.g., while folding the balloon in the manufacturing process the balloon will maintain its shape if the "wings" of the folded jacket will remain tight).

Catheter 210m may be advanced towards the treatment site over guide wire 253 threaded through the lumen of inner shaft 257. Catheter 210m is preferably placed adjacent to occlusion 270, preferably such that its distal tip 201 contacts said occlusion. Once catheter 210m is placed in the treatment site balloon 205aa may be inflated by introducing pressurized inflation media (designated by arrows 208a) via inflation port 251. Inflation media is passed via inflation fluid lumen defined between inner wall of outer shaft 258 and the outer surface of inner shaft 257. In its inflated state (FIG. 12B) lateral sides of the backwardly folded balloon 205aa are pressed against the inner wall 221 of vessel 260, thereby anchoring it thereto. Due to its initial folded state the distal end of the inflated balloon gains a rounded shape, as shown in FIG. 12B.

At this state point, distal end 201 of inner shaft 257 may be vibrated about its longitudinal axis by applying an oscillatory pressure source for periodically changing the pressure of the inflation media in balloon 205aa. Such periodical pressure changes cause corresponding lengthening and shortening of balloon 205aa and elastic inner shaft 257 (or elastic portions thereof 255) which may be employed for rupturing the occlusion and thereby opening a passage pathway therethrough.

The operator may advance guidewire 253 such that distal end portions thereof may leave inner shaft 257 through its distal end opening, e.g., such that 1 to 5 mm of the wire protrudes from the distal end of the catheter, as demonstrated in FIG. 12B. This is preferably carried out by advancing proximal portions of guidewire 253 distally through proximal end opening 252 of inner shaft 257 such that a distal portion thereof protrudes outwardly via the proximal end opening (at distal tip 201) of inner shaft 257.

Figure 13A:
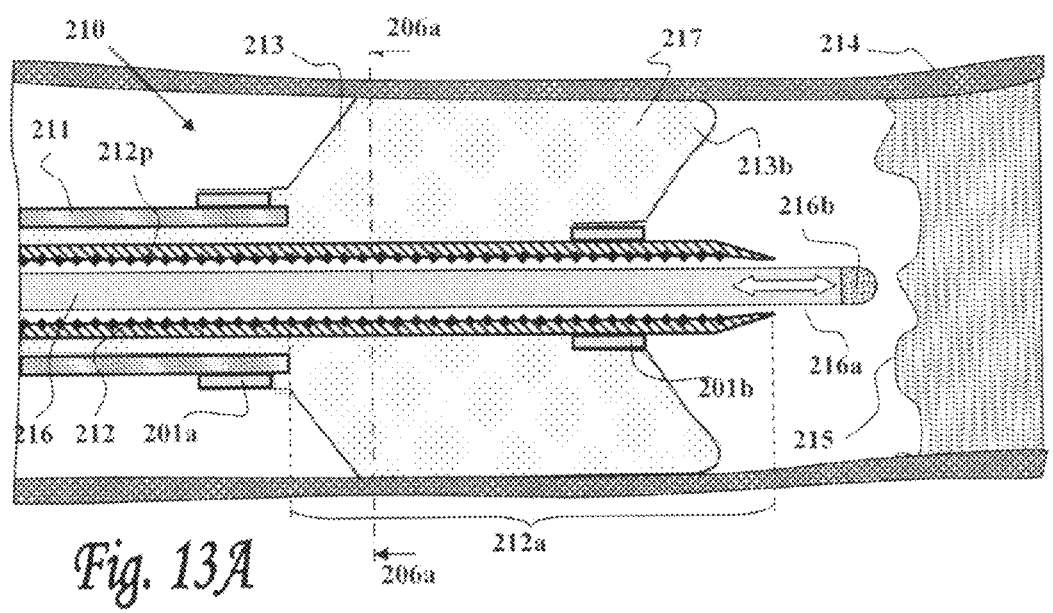
FIGS. 13A and 13B are longitudinal and cross-sectional views illustrating a balloon catheter device of the invention that is capable of delivering rapid motion to its distal end portion and to a guidewire passing therein.
Figure 13B:
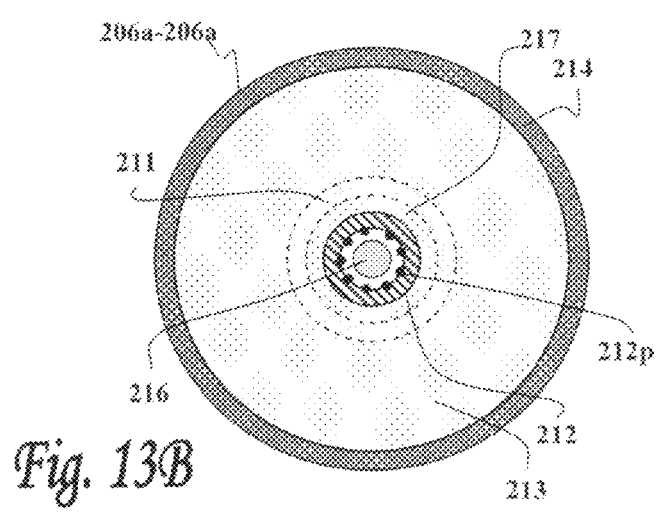

FIGS. 13A and 13B schematically illustrate a preferred embodiment of the balloon catheter device 210 of the invention operatively situated in an occluded body passageway 214 (e.g., blood vessel) comprising occluding matter 215. Balloon catheter 210 comprises an inflatable member 213 attached in a proximal attachment 201a to a distal end portion of outer tube 211 of balloon catheter device 210, and in a distal attachment 201b to a distal end portion of inner tube 212 passing in outer tube 211.

Inflatable member 213 is preferably made from a non-compliant or semi-compliant sleeve having tapering extremities that are adapted to fit over the outer surfaces of outer and inner tubes, 211 and 212. Inflatable member 213 is configured to perform radial expansion, when filled with a suitable inflation media 217, and thereafter distal expansion of its distal portion 213b, when said inflation media 217 is pressurized. As demonstrated in the longitudinal and cross-sectional views of the catheter device 210 shown in FIGS. 13A and 13B, radial expansion of inflatable member 213 presses its lateral wall against the inner side of the body pathway or organ 214 in which it is placed and thereby centers and anchors catheter device 210 in place.

Inner shaft tube 212 can be affixed to the outer shaft tube 211, or it may be reversibly attached to it via releasable locking means (not shown) provided at a proximal portion thereof, such that a distal portion 212a of inner tube 212 protrudes outwardly via the distal end opening of outer tube 211. At least a portion of inner tube 212 is elastically deformable to allow distal elongation thereof in response to distal expansions of inflatable member 213. For example, inner tube 212, or a portion thereof, may be manufactured from an elastic material (e.g., Pebax and/or Nylon Blend), or from a soft and flexible material comprising an elastic element such as a spring. Various ways of making a section of the inner tube elastically deformable are described in U.S. application No. 60/726,180 and in international patent application no. . . . of the same applicant hereof, the disclosure of which is hereby incorporated by reference.

In a preferred embodiment of the invention inflatable member 213 is made from a non-compliant or a semi-compliant sleeve having tapering ends designed to fit over the outer surfaces of inner tube 212 and outer tube 211. The inner surface of the proximal end of the flexible sleeve is fitted and attached on the outer surface of a distal end portion of outer tube 211 at proximal attachment 201a, and the outer surface of the distal end of the flexible sleeve is fitted and attached on the outer surface of a distal end portion of outer tube 211 at distal attachment 201b.

The location of distal attachment 201b on distal portion 212a of inner tube 212 is chosen such that distal end portions of inflatable member 213 are folded proximally inwardly over a distal end portion of inner tube 212. In this way distal expansion of distal portion 213b of inflatable member 213 is achieved by increasing the pressure of the inflation media 217 inside inflatable member 213 which in response force the inwardly folded distal portions of inflatable member 213 to unfold distally and restore the original shape of inflatable member 213, thereby increasing the volume of inflatable member 213 and stretching distal portion 212a of outer tube 212 distally, as demonstrated in FIG. 14A.

Figure 14A:
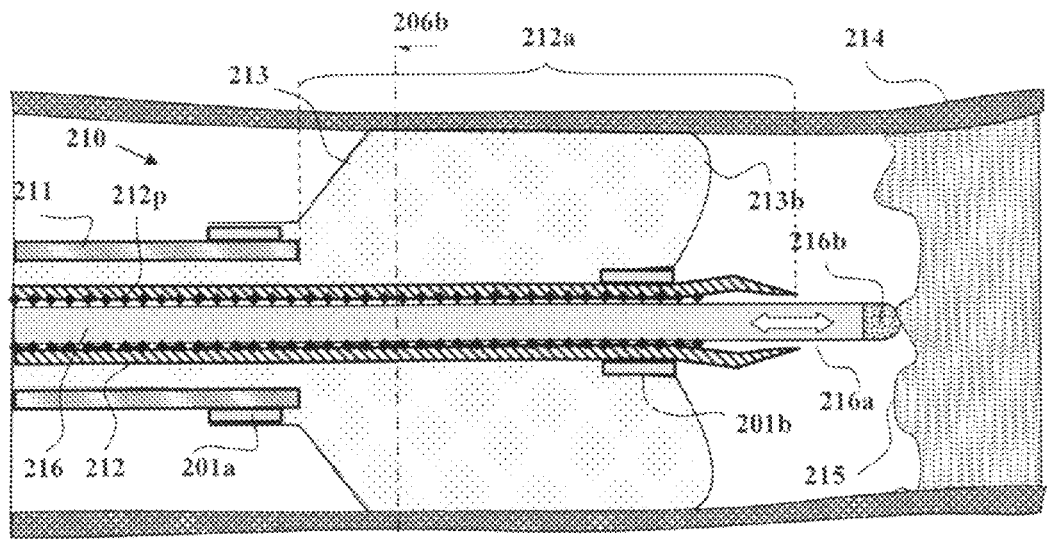
FIGS. 14A and 14B are longitudinal and cross-sectional views illustrating the balloon catheter device of the invention ramming an occlusion.
Figure 14B:
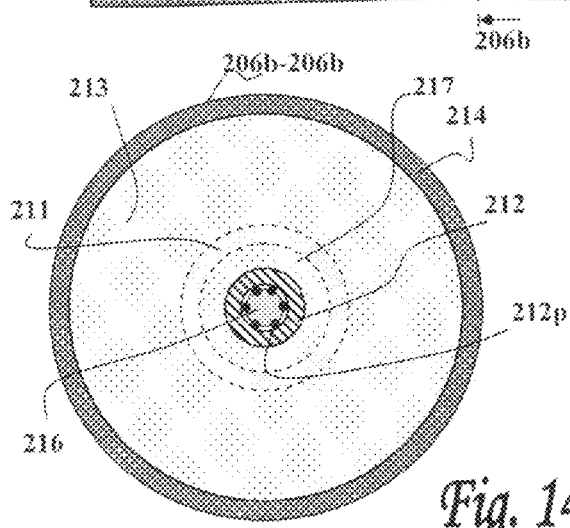

A ramming tool 216 (e.g., guidewire) passing in the lumen of inner tube 212, and mechanically coupled thereto, is used for the fracturing and/or tunneling of occlusion 215, as shown in FIGS. 14A and 14B. The mechanical coupling between ramming tool 216 and inner tube 212 may be achieved by making distal portion of inner tube 212 from a flexible material capable of being pressed over, and thereby retain, a portion of ramming tool 216 passing thereinside.

The inner surface of inner tube 212 may be roughened in order to increase its friction constant for enhancing the gripping forces that may be applied by it upon ramming tool 216. For example, the roughening to the inner surface of inner tube 212 may be obtained by forming (or attaching) protrusions 212p thereon (e.g., by a chemical process, such as chemical deposit of particles on the exposed inner wall of the tube).

Outer tube 211 may be manufactured by extrusion from a polymeric material, such as Nylon, preferably from Polyurethane. The inner diameter of outer tube 211 may generally be in the range of 0.4 to 1.0 mm, preferably about 0.75 mm, and its length may generally be in the range of 1000 to 2000 mm, preferably about 1500 mm.

Inner tube 212 may be manufactured by extrusion from a metallic material, such as stainless steel, preferably from SS 316, to which one or more elastic distal end portions may be attached, as will be exemplified herein later. The inner diameter of proximal inner tube 212 may generally be in the range of 0.2 to 0.8 mm, preferably about 0.4 mm, and its length may generally be in the range of 1000 to 2000 mm, preferably about 1450 mm. The length of distal portion 212a of inner tube 212 protruding outwardly via the distal end opening of outer tube 211 is generally in the range of 5 to 30 mm, preferably about 10 mm.

In a preferred embodiment of the invention the length of distal portion 212a of inner tube 212 may be adjusted by the operator via releasable immobilizing means (not shown) provided at a proximal end portion of the device, that allows the operator to move inner tube 212 distally/proximally and affix it to outer tube 211 at a desired location. In such implementation the operation of the balloon catheter may be divided into a number of stages in which the length of distal portion 212a of inner tube 212 is gradually increased according to the progress of the perforation (or tunneling) performed in occlusion 215.

Inflatable member 213 may be manufactured by blowing from a polymeric material, such as Nylon, preferably from a Nylon-Pebax blend. The diameter of inflatable member 213 may generally be in the range of 1.5 to 8 mm, preferably about 3 mm, and its length may generally be in the range of 10 to 50 mm, preferably about 20 mm. Attachment of inflatable member 213 to inner and outer tubes 212 and 211, at distal and proximal attachments 21b and 21a, respectively, may be achieved by means of bonding, preferably by thermal bonding process.

Inflation media 217 may be any type of conventional inflation media used in balloon catheters. For example, a type of Saline or image contrast fluid. The pressure in inflatable member 213 when first inflated to an anchoring pressure in order to anchor catheter device 210 in place, is generally in the range of 1 to 6 atmospheres. When the inflation media 217 in inflatable member 213 is further pressurized, for effecting distal expansions of distal portion 213b, the inflatable media 217 is further pressurized to a pressure generally in the range of 1 to 10 atmospheres. The time intervals in which the inflation media 217 is repeatedly pressurized for effecting said distal expansions of distal portion 213b may be varied according to the type of occlusion to be opened. For example, in a specific embodiment of the invention the pressure of the inflation fluid 217 may be periodically changed between 6 and 8 atmospheres in frequencies in the range of 1 to 20 Hz, preferably about 10 Hz.

The elongation of inner tube 212 may generally be in the range of 0.5 to 3 mm, preferably about 1 mm. The diameter of ramming tool/guidewire 216 may generally be in the range of 0.009 inch to 0.035 inch, preferably about 0.014 inch, and its length may generally be in the range of 180 to 250 mm, preferably about 190 mm.

Figure 15:
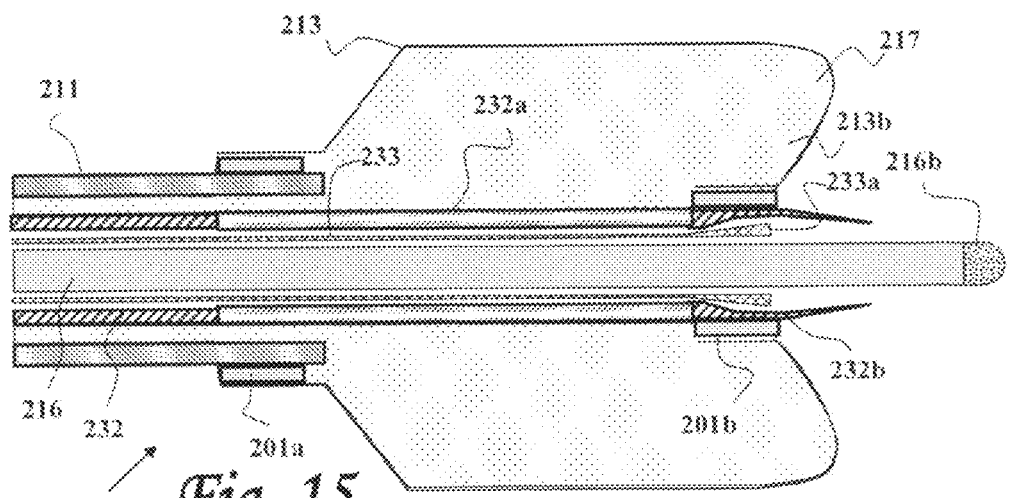
FIG. 15 schematically illustrate the balloon catheter device of the invention comprising coupling means between the inner tube and the ramming tool (guidewire)

FIG. 15 illustrates an implementation of a balloon catheter 230 wherein the catheter comprises coupling means for strengthening the grip of the distal portion of the inner tube over ramming tool (guidewire) 216. The coupling means comprise pull member 233 disposed in inner tubes 232 along partial (or entire) length thereof. The distal end of pull member 233 preferably comprises wedge shaped locking member 233a. The distal end section 232b of inner tube 232 may be configured accordingly to comprise said wedge shaped locking member 233a thereinside, as shown in FIG. 15. As may be seen in FIG. 15, the inner diameter of said distal end section 232b is greater near the distal tip and it is gradually decreased towards the proximal end of the distal end section 232b.

The coupling means implemented by pull member 233 enhances the grip of inner tube 232 over ramming tool (guidewire) 216, particularly during distal expansions of inflatable member 213, as occurring during repeated distal expansions of inflatable member 213. During said distal expansions the pressure in inflatable member 213 is increased which in turn stretches flexible section 232a distally. Distal stretch of flexible section 232a cause in turn distal movement of distal end section 232b of inner tube 232 which locks wedge shaped locking member 233a due to its tapering inner shape, and thus forces wedge shaped locking member 233a to grip ramming tool 216.

Flexible section 232a can be made of an elastic material, such as Pebax, and it may be embedded into a distal portion of inner tube 232, by thermal bonding. The length of flexible section 232a may generally be in the range of 10 to 100 mm, preferably about 80 mm. Wedge shaped locking member 233a can be made of a metallic material, such as stainless steel, and it may be combined or installed in inner tube 232 by adhesives. The length of wedge shaped locking member 233a may generally be in the range of 1 to 3 mm, preferably about 2 mm, and its diameter should be slightly greater than the diameter of ramming tool (guidewire) 216.

Figure 16:
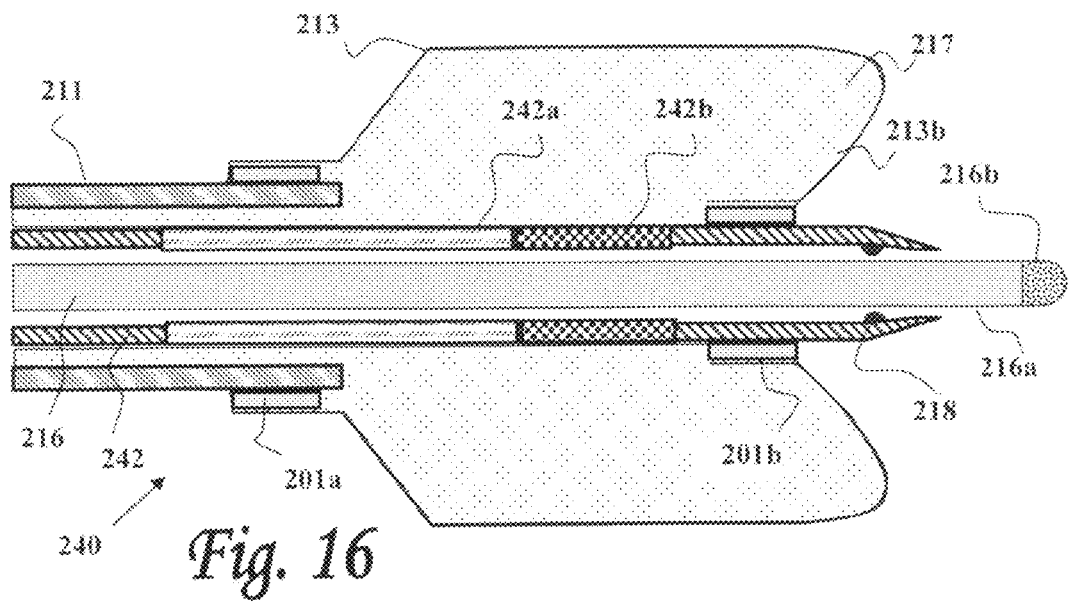
FIG. 16 schematically illustrates another possible coupling means between the inner tube and the ramming tool (guidewire)

FIG. 16 illustrates an implementation of a balloon catheter 240 wherein the inner tube 242 comprises an elastic section 242a in which coupling means 242b are provided for establishing a grip over ramming tool (guidewire) 216. Elastic section 242a is configured to permit lengthening and retraction of the distal end section of the inner tube 242 during oscillatory pressure changes in inflation media 217. Coupling means 242b is preferably made from a soft and flexible material (e.g., elastomers) embedded in the distal end section of elastic section 242a for gripping ramming tool (guidewire) 216 during pressure increments in inflation media 217.

In one preferred embodiment, the operation of the balloon catheter of the invention comprises the steps of:
i) inserting the distal end of a pre-charged balloon catheter 240 into the treatment site such that its distal tip is placed in the vicinity (e.g., 1 to 5 mm) of the occluding matter 215;
ii) inflating the inflatable member 213 with a suitable inflation media 217 pressurized to about 1 atmospheres to anchor and center the distal end section of the balloon catheter in place;
iii) optionally, manually ramming the distal tip 216b of the ramming tool 216 into the occluding matter, by pulling and pushing it at its proximal end, and if such manual operation is not sufficient for passing the occlusion;
iv) advancing ramming tool 216 distally such that a distal end portion thereof (e.g., about 1-5 mm) protrudes distally via the distal end opening of inner tube;
v) pressurizing the inflation media 217 to about 2 atmospheres which in turn causes distal expansion of the distal section 213b of the inflatable element 213 thereby causing stretching and lengthening of coupling means 242b which in turn results in it being tightly pressed over ramming tool (guidewire) 216. In this way the stretching and lengthening of coupling means 242b is utilized to press its wall over ramming tool 216, thereby gripping said tool;
vi) pressurizing the inflation media 217 to about 4 atmospheres which in turn causes distal expansion of the distal section 213b of the inflatable element 213, which in turn causes stretching and lengthening of elastic section 242a, and moves the distal end section of ramming tool (guidewire) 216 distally such that its distal tip 216b is rammed into the occluding matter 215;
vii) reducing the pressure of the inflation media 217 back to about 2 atmospheres which causes elastic section 242a to return to its un-stretched length and inwardly fold back the distal section 213b of inflatable element 213, while maintaining a tight grip of coupling means 242b over ramming tool (guidewire) 216 thereby retracting it proximally; and
viii) repeating steps vi) and vii) in an oscillatory manner at a frequency of between 1 to 20 Hz, preferably about 10 Hz, until the desired perforation of the occluding material is achieved;
ix) advancing the ramming tool (guidewire) distally until it passes through the occluding matter and thereby providing a passage therethrough; and optionally
x) carrying out a conventional treatment suitable for opening the occlusion (e.g., balloon inflation, stenting, and/or any other technique well known to the skilled artisan.)

In a modification of the basic operating procedure described immediately hereinabove, the pressure levels of the inflation media may be manipulated such that a "ratchet mechanism" is created, thereby automatically advancing the wire inside the occlusive material. This is achieved by means of cyclically reducing the pressure to below the grasping pressure reached in step (v) of the procedure described above (e.g. to below a level of about 2 atmospheres), and then elevating the pressure to a level above said grasping pressure. In this way, the guide wire is released from being grasped by the inner shaft (when the pressure is lowered to beneath grasping pressure), and then re-grasped at a more proximal point along its length, thereby advancing the distal tip of the wire towards or inside the occluding material.

The advantage of this modified mechanism is the automatic advancement of the guide wire thereby obviating the need for manually reducing the pressure inside the balloon in order to release the grasp, and then manually advancing the guide wire and repeating the grasping phase (step v) at a more proximal location, followed by the stretching phase (step vi).

There are a number of different ways in which the above-described ratchet effect may be implemented. These include (but are not limited to) the following embodiments:
1) The operator maintains manual pressure on the proximal end of the guide wire while the cyclic pressure changes of the ratchet mechanism (as described above) are continued. In this way, the guide wire is released from being grasped by the inner shaft (when the pressure is lowered to beneath grasping pressure), and then re-grasped at a more proximal point along its length,
2) As the guide wire begins to negotiate its way through the lesion, frictional forces that act on the guide wire's distal end prevent the ratchet mechanism from withdrawing the guide wire (i.e. in a proximal direction. In this way, the guide wire is released from being grasped by the inner shaft (when the pressure is lowered to beneath grasping pressure), and then re-grasped at a more proximal point along its length,
3) The guide wire passes through a friction-generating element on the proximal end of the catheter, such that the friction forces thereby generated at said proximal end prevent the ratchet mechanism from causing the reciprocal (i.e. proximal) movement of the guide wire in the same displacement. In one embodiment, the friction-generating element is provided in the form of a friction controllable annular clamp attached to the proximal end of the catheter shaft, surrounding the guidewire as it moves through its lumen, thereby slightly inhibiting said movement.

In the case of balloon catheters utilizing non-charged balloons, the above-described basic procedure may be employed with the addition of the following step: after anchoring of the balloon at the treatment site (step (ii)), the operator may manipulate the inflated balloon by releasing a grasping element (immobilizer), thus allowing the inner shaft to be moved proximally relative to the outer shaft. The inner shaft is then retracted proximally and anchored at its new location by re-applying the grasping element. This step is described in more detail hereinabove in relation to the implementation of the device exemplified in FIG. 11C.

Optionally, following step viii) and prior to step ix), the following steps may be performed:
A) stopping the repeated pressure pulses (steps vi and vii), reducing the pressure of the inflation media 217 to about 1 atmospheres and releasing inner tube immobilizer to increase the length of distal portion 212a in order to change the state of inflatable member into a second folded state in which a smaller portion of the length of inflatable member 213 is folded proximally inwardly;
B) restoring grasping pressure of inflation media in inflatable member, restoring immobilization of the inner tube, and applying the repeated pressure pulses (steps vi and vii) using similar frequencies within a similar period of time;
C) repeating steps A) and B) to apply the repeated pressure pulses in a third folded state (e.g., smaller length of inflatable member 213 is folded proximally inwardly);

Elastic section 242a may be manufactured by extrusion from a polymeric material, such as Nylon blend, preferably from Pebax-Nylon blend. The length of elastic section 242a may generally be in the range of 10 to 100 mm, preferably about 80 mm, and it may be attached to inner tube 242 (e.g., thermal bonding and/or Induction bonding).

Coupling means 242b may be implemented using a soft material such as silicone or polymer, and/or by embedding a braided section in flexible section 242b. The grip applied by coupling means 242b may be further enhanced by coating its inner surface with friction enhancing material, such as silicon coating, by embedding an inner silicone tube segment or a coil in elastic section 242b. Additionally or alternatively, coupling means 242b may have a rectangular cross-sectional shape in order to increase buckling thereof, and thus enhance its grip, when it is pressed against ramming tool (guidewire) 216.

The coupling means may further comprise gripping protrusions 218 attached to, or formed on, the inner wall of inner tube 242, near its distal tip. Gripping protrusions 218 are configured to be in contact with the surface (216a) of ramming tool (guidewire) 216 and thus grip its distal end section during elongation and retraction of inner tube 242a. Gripping protrusions 218 are configured to allow enhanced pushing/pulling forces exerted from the proximal end of ramming tool 216 to overcome the friction forces between gripping protrusions 218 and ramming tool (guidewire) 216 in order to permit re-positioning and advancing ramming tool 216 distally such that a distal end portion thereof protrudes distally via the distal end opening of inner tube.

Figure 17:
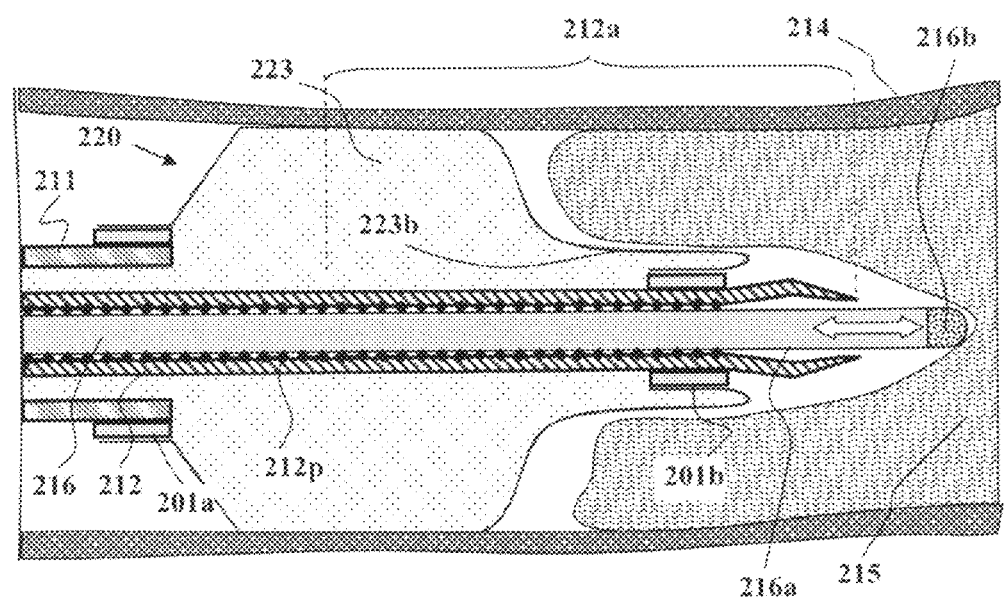
FIG. 17 schematically illustrates a balloon catheter of the invention wherein the inflatable member comprises a narrow distal portion.

FIG. 17 illustrates a preferred embodiment of a balloon catheter 220 of the invention wherein a distal end portion 223b of inflatable member 223 is made narrow. The structure and principal of operation of balloon catheter 220 are substantially similar to those of balloon catheter 210 described with reference to FIGS. 13A, 13B, 14A and 14B. However, due to its narrow distal end section 223b, inflatable member 223 of balloon catheter 220 may be advanced into perforated portions of occlusion 215, as demonstrated in FIG. 17.

The diameter of inflatable member 223 may generally be in the range of 1.5 to 6 mm, preferably about 3 mm, and its length in the range of 10 to 50 mm. The diameter of narrow distal end section 223b of inflatable member 223 may generally be in the range of 1 to 3 mm, preferably about 1 mm, and its length in the range of 5 to 20 mm.

It is to be noted that the second main embodiment of the device of the present invention may be implemented in the same variants as discussed in relation to the first main embodiment, hereinabove, namely over the wire implementations (as depicted in FIGS. 11 to 17), rapid exchange catheters (incorporating the rapid exchange features depicted in FIG. 2) and bitumen catheters (as depicted in FIGS. 9A and 9B).

Figure 18A:
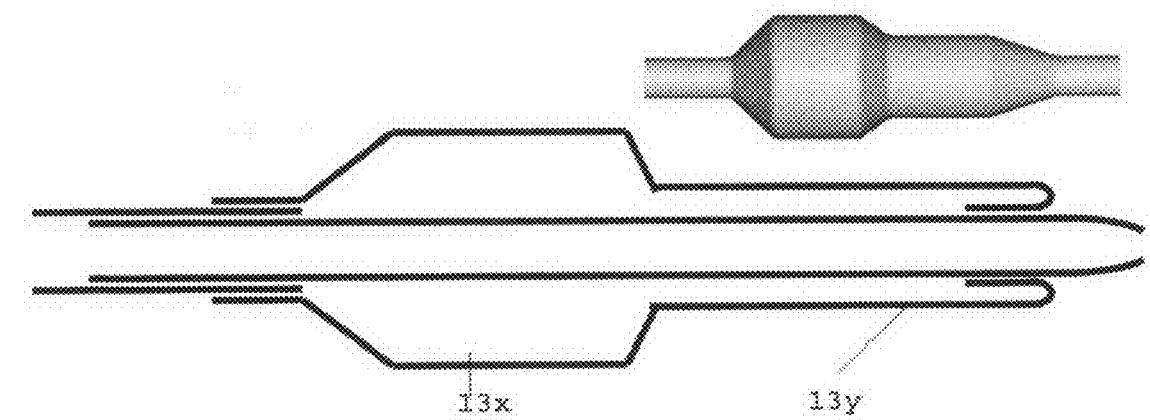
FIGS. 18A and 18B illustrate two alternative embodiments that may be used when there is a need to maneuver the balloon catheter through a curved region of the vasculature.

FIG. 18A depicts an alternative embodiment of balloon 13, which may be advantageously used in conjunction with either of the main embodiments of the device of the present invention when the balloon catheter needs to negotiate a curve or bend in the blood vessel which is being treated. This embodiment of the balloon is constructed such that it possesses a stepped shape, having a broader proximal portion 13x and a narrower distal portion 13y. As the balloon is advanced towards the curved region of the blood vessel, the narrow distal balloon portion 13y enabling the catheter and guide wire tips to be centered within said curved or arched region. This balloon design may also be used as a deflectable catheter, wherein the narrow distal portion 13y is manually diverted towards the occlusion, centering the tip with respect to vessel geometry.

Figure 18B:
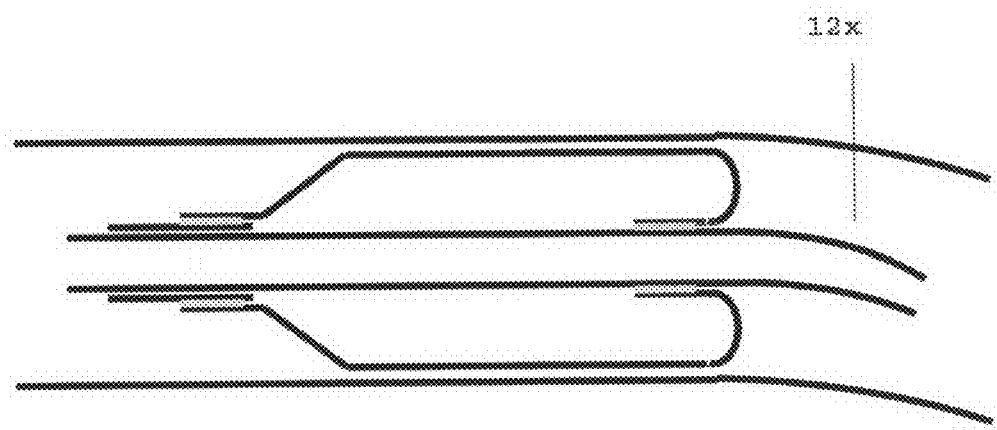

FIG. 18B depicts a further, alternative embodiment that may also be used to negotiate curved or arched regions of the vasculature. In this embodiment, the distal end of the inner shaft of the catheter beyond the distal end of the balloon 12x is considerably longer than in the embodiments hereto described, thereby permitting manually diversion of this extension around the arched portion of the blood vessel.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different shafts and tubes, and other members, described hereinabove may be constructed in different shapes (e.g. having oval, square etc. form in plan view) and sizes from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A balloon catheter comprising:
    a hollow inner shaft disposed within a hollow outer shaft such that the distal end of the inner shaft extends beyond the distal end of the outer shaft, wherein the lumen of said inner shaft is suitable for allowing the passage of a guidewire through all or part of its length;
    a balloon attached at its proximal end to said outer shaft and at its distal end to said inner shaft; and
    wherein an inflation fluid is adapted to be introduced into the annular space formed between the inner surface of the outer shaft and the outer surface of the inner shaft and therefrom into the lumen of said balloon, and for the removal thereof;
    wherein the inner shaft is constructed such that following radial expansion of the balloon to a first expanded state, said inner shaft is capable of responding to further longitudinal expansion of the balloon to a second expanded state by increasing its length from a resting value, and of responding to subsequent partial deflation back to said first expanded state by reducing its length back to said resting value; and
    wherein the balloon is attached at its distal end to said inner shaft in an intussuscepted manner or the balloon is attached at its distal end to said inner shaft in a non-intussuscepted manner but distal intussusception may be created by moving the inner shaft in a proximal direction during operation of the balloon catheter.

2. The balloon catheter according to claim 1, wherein the inner shaft comprises at least one portion that is elastically deformable.

3. The balloon catheter according to claim 2, wherein, following radial expansion of the balloon to a first expanded state, said elastically deformable portion of the inner shaft is capable of responding to further longitudinal expansion of the balloon to a second expanded state by increasing its length from a resting value, and of responding to subsequent partial deflation back to said first expanded state by reducing its length back to said resting value.

4. The balloon catheter according to claim 1, wherein the distance between the points of attachment of the balloon to the inner and outer shafts is less than the overall length of the balloon.

5. The balloon catheter according to claim 2, wherein the at least one elastically deformable portion is constructed of a blend of nylon and Pebax.

6. The balloon catheter according to claim 1, wherein the balloon is attached at its distal end in an inverted manner, such that the external surface of said balloon is in contact with, and attached to, the outer surface of the inner shaft.

7. The balloon catheter according to claim 1, wherein said catheter is constructed as an over-the-wire catheter.

8. The balloon catheter according to claim 1, wherein the inner shaft is capable of being moved along its longitudinal axis in relation to the outer shaft, and wherein said catheter is adapted to immobilize said inner shaft.

9. The balloon catheter according to claim 1, wherein said catheter is constructed as a rapid exchange catheter.

10. A balloon catheter comprising a conduit having a proximal portion and a distal portion,
wherein said proximal portion contains two separate lumens, one of said lumens being suitable for allowing the passage of a guidewire therethrough, the other lumen being suitable for allowing passage of a fluid,
wherein said distal portion is a single-lumen conduit that is in fluid communication with the guidewire lumen of said proximal portion,
wherein a balloon is attached at its proximal end to the outer surface of said proximal portion and at its distal end to said distal portion, and
wherein a connecting tube segment is positioned between said proximal portion and said attachment point of said proximal end of said balloon,
wherein at least part of said distal portion is constructed such that following radial expansion of the balloon to a first expanded state, said distal conduit portion is capable of responding to further expansion of the balloon to a second expanded state by increasing its length from a resting value, and of responding to subsequent partial deflation back to said first expanded state by reducing its length back to said resting value, and
wherein the balloon is attached at its distal end in a non-inverted manner, such that the internal surface of said balloon is in contact with, and attached to, the outer surface of the inner shaft.

11. The balloon catheter according to claim 10, wherein the proximal neck of the balloon is extended as compared to conventional angioplasty balloons, such that the length of the distal conduit may be correspondingly extended.

12. The balloon catheter according to claim 10,
wherein the catheter further comprises a connecting tube segment positioned between the conduit proximal portion and the proximal balloon neck, thereby forming a middle portion,
wherein said middle portion comprises two concentrically arranged conduits, the lumen of the outer of said concentrically arranged conduits being in fluid communication with the fluid passage lumen of said proximal portion, the inner of said concentrically arranged conduits being formed by the distal conduit,
and wherein the lumen of said distal conduit is in fluid communication with the guidewire lumen of said proximal portion, the connecting tube segment having a proximal end attached to the distal end of the proximal portion, and a distal end attached to the balloon proximal neck.

13. The balloon catheter according to claim 10, wherein the distal portion of the conduit comprises at least one portion that is elastically deformable.

14. The balloon catheter according to claim 13, wherein the at least one elastically deformable portion is constructed of a blend of nylon and Pebax.

15. A balloon catheter comprising:
an inner shaft disposed within an outer shaft such that the distal end of the inner shaft extends beyond the distal end of the outer shaft, wherein the lumen of said inner shaft is suitable for allowing the passage of a guidewire through all or part of its length;
a balloon attached at its proximal end to said outer shaft and at its distal end to said inner shaft;
a supplementary guide wire grasping element; and
wherein an expansion fluid is adapted to be introduced into the annular space formed between the inner surface of the outer shaft and the outer surface of the inner shaft and therefrom into the lumen of said balloon, and for the removal thereof;
wherein the inner shaft is constructed such that following radial expansion of the balloon to a first expanded state, a portion of said inner shaft is capable of responding to further longitudinal expansion of the balloon to a second expanded state by reducing its inner diameter thereby being able to grasp a guidewire placed within the lumen of said inner shaft, thereby preventing movement of said guidewire relative to said inner shaft, and such that said inner shaft is capable of responding to further expansion of the balloon from said second expanded state to a third expanded state by increasing its length from a resting value, and of responding to subsequent partial deflation back to said second expanded state by reducing its length back to said resting value.

16. The balloon catheter according to claim 15, wherein the inner shaft comprises at least a first elastically deformable portion and second elastically deformable portion, wherein, following radial expansion of the balloon to a first expanded state,
said first elastically deformable portion of the shaft is capable of responding to further longitudinal expansion of the balloon to a second expanded state by reducing its inner diameter thereby being able to grasp a guidewire placed within the lumen of said inner shaft and thereby preventing movement of said guidewire relative to said inner shaft,
and wherein said second elastically deformable portion of the shaft is capable of responding to further longitudinal expansion of the balloon from said second expanded state to a third expanded state by increasing its length from a resting value, and of responding to subsequent partial deflation back to said second expanded state by reducing its length back to said resting value.

17. The balloon catheter according to claim 15, wherein the distance between the points of attachment of the balloon to the inner and outer shafts is less than the overall length of the balloon when said balloon is in the first expanded state.

18. The balloon catheter according to claim 15, wherein the proximally-located and distally-located elastically deformable portions are each constructed of blends of nylon and Pebax.

19. The balloon catheter according to claim 15, wherein the supplementary guide wire grasping element comprise protrusions on the inner wall of the inner shaft.

20. The balloon catheter according to claim 15, wherein the supplementary guide wire grasping element comprise wedge-shaped locking element.

21. The balloon catheter according to claim 15, wherein the balloon is attached at its distal end in an inverted manner, such that the external surface of said balloon is in contact with, and attached to, the outer surface of the inner shaft.

22. The balloon catheter according to claim 15, wherein the balloon is attached at its distal end in a non-inverted manner, such that the internal surface of said balloon is in contact with, and attached to, the outer surface of the inner shaft.

23. The balloon catheter according to claim 15, wherein said catheter is constructed as an over-the-wire catheter.

24. The balloon catheter according to claim 15, wherein the inner shaft is capable of being moved along its longitudinal axis in relation to the outer shaft, and wherein said catheter is adapted to immobilize said inner shaft.

25. The balloon catheter according to claim 15, wherein said catheter is constructed as a rapid exchange catheter.

26. The balloon catheter according to claim 15, wherein the proximal end of said catheter further comprises a friction-generating element that is capable of applying frictional forces to the proximal region of a guide wire placed within a lumen of said catheter.

27. A balloon catheter comprising a conduit having proximal and distal portions,
wherein said proximal portion contains two separate lumens, one of said lumens being suitable for allowing the passage of a guidewire therethrough, the other lumen being suitable for allowing passage of a fluid,
wherein said distal portion contains a single lumen, said lumen being the continuation of the guidewire lumen,
wherein a balloon is attached at its proximal end to said proximal conduit portion and at its distal end to said distal conduit portion;
and wherein the distal portion of the conduit is constructed such that following radial expansion of the balloon to a first expanded state, a portion of said distal conduit portion is capable of responding to further longitudinal expansion of the balloon to a second expanded state by reducing its inner diameter thereby being able to grasp a guidewire placed within the lumen of said distal conduit portion, thereby preventing movement of said guidewire relative to said inner shaft, and such that
said distal conduit portion is capable of responding to further expansion of the balloon from said second expanded state to a third expanded state by increasing its length from a resting value, and of responding to subsequent partial deflation back to said second expanded state by reducing its length back to said resting value, and
wherein the balloon is attached at its distal end to said distal portion of the conduit in an intussuscepted manner or the balloon is attached at its distal end to said distal portion of the conduit in a non-intussuscepted manner but distal intussusception may be created by moving the distal end of the conduit in a proximal direction during operation of the balloon catheter.

28. The balloon catheter according to claim 27, wherein the distal portion of the conduit comprises at least one portion constructed of at least two different shaped elastically deformable segments.

29. The balloon catheter according to claim 28, wherein the elastically deformable portions are constructed of blends of nylon and Pebax.

30. A balloon catheter comprising a conduit having a proximal portion, a middle portion and a distal portion,
wherein said proximal portion contains two separate lumens, one of said lumens being suitable for allowing the passage of a guidewire therethrough, the other lumen being suitable for allowing passage of a fluid,
wherein said middle portion contains two concentrically arranged conduits, the lumen of the outer conduit being in fluid communication with the fluid passage lumen of said proximal portion, the lumen of the inner conduit being in fluid communication with the guidewire lumen of said proximal portion,
wherein said distal portion is a single-lumen conduit that is in fluid communication with the inner lumen of said middle portion,
wherein a balloon is attached at its proximal end to the outer surface of said middle portion and at its distal end to said distal portion;
wherein said balloon is a stepped balloon;
and wherein at least part of the distal portion is constructed such that following radial expansion of the balloon to a first expanded state, said distal portion conduit is capable of responding to further expansion of the balloon to a second expanded state by reducing its inner diameter thereby being able to grasp a guidewire placed within the lumen of said distal conduit portion, thereby preventing movement of said guidewire relative to said inner shaft, and such that
said middle portion inner conduit is capable of responding to further expansion of the balloon from said second expanded state to a third expanded state by increasing its length from a resting value, and of responding to subsequent partial deflation back to said second expanded state by reducing its length back to said resting value.

31. The balloon catheter according to claim 30, wherein the middle portion inner conduit or said distal portion of the conduit comprises at least one distinct portion that is elastically deformable.

32. The balloon catheter according to claim 30, wherein the stepped balloon has a broader proximal portion and a narrower distal portion.

* * * * *